US009757302B2

(12) United States Patent
Mayer

(10) Patent No.: US 9,757,302 B2
(45) Date of Patent: Sep. 12, 2017

(54) FOOT COMPRESSION AND ELECTRICAL STIMULATION SYSTEM

(71) Applicant: Avex, LLC, Grand Junction, CO (US)

(72) Inventor: Matthew J. Mayer, Grand Junction, CO (US)

(73) Assignee: AVEX, LLC, Grand Junction, CO (US)

( * ) Notice: Subject to any disclaimer, the term of this patent is extended or adjusted under 35 U.S.C. 154(b) by 219 days.

(21) Appl. No.: 14/178,554

(22) Filed: Feb. 12, 2014

(65) Prior Publication Data

US 2014/0213940 A1    Jul. 31, 2014

Related U.S. Application Data

(63) Continuation of application No. PCT/US2012/050290, filed on Aug. 10, 2012.
(Continued)

(51) Int. Cl.
*A61H 1/00* (2006.01)
*A61N 1/04* (2006.01)
(Continued)

(52) U.S. Cl.
CPC .......... *A61H 1/008* (2013.01); *A61N 1/0452* (2013.01); *A61N 1/0484* (2013.01);
(Continued)

(58) Field of Classification Search
CPC .............. A61H 2201/10; A61H 39/002; A61H 2201/165
(Continued)

(56) References Cited

U.S. PATENT DOCUMENTS 1,546,506 A    7/1925    Naysmith
2,397,428 A    3/1946    Moshier
(Continued)

FOREIGN PATENT DOCUMENTS

AT    506689    11/2009
CN    2476275    2/2002
(Continued)

OTHER PUBLICATIONS

Notice of Allowance dated Apr. 12, 2012 for U.S. Appl. No. 13/004,754.
(Continued)

*Primary Examiner* — Amanda Patton
*Assistant Examiner* — Philip C Edwards
(74) *Attorney, Agent, or Firm* — Snell & Wilmer L.L.P.

(57) ABSTRACT

Systems configured to apply pressure to a foot and electrically stimulate muscles to contract in order to increase circulation and facilitate removal of metabolic waste, and related methods, are disclosed. One exemplary embodiment comprises an actuator that repeatedly compresses the bottom of a foot and an electrical muscle stimulator that repeatedly sends electrical pulses to a muscle to facilitate a muscle contraction. The system may also include a compression garment, such as a compression sock to be worn while undergoing both the repeated compression cycles and the repeated electrical pulses. The system may also include an item of footwear, wherein the actuator portion is partially or completely contained within the item of footwear. Additionally and/or alternatively, the electrical muscle stimulator may be partially or completely contained within the item of footwear.

18 Claims, 15 Drawing Sheets

Related U.S. Application Data

(60) Provisional application No. 61/523,023, filed on Aug. 12, 2011.

(51) Int. Cl.
*A61N 1/32* (2006.01)
*A61N 1/36* (2006.01)

(52) U.S. Cl.
CPC .......... *A61N 1/0492* (2013.01); *A61N 1/322* (2013.01); *A61N 1/36003* (2013.01); *A61N 1/36014* (2013.01)

(58) Field of Classification Search
USPC ........................................................ 601/21
See application file for complete search history.

(56) References Cited

U.S. PATENT DOCUMENTS

| | | |
|---|---|---|
| 2,836,174 A | 5/1958 | Infanger |
| 3,612,043 A | 10/1971 | Inaki |
| 3,888,242 A | 6/1975 | Harris et al. |
| 3,917,261 A | 11/1975 | Small et al. |
| 4,166,329 A | 9/1979 | Herbig |
| 4,294,236 A | 10/1981 | Hofstein |
| 4,299,206 A | 11/1981 | Hofstein |
| 4,721,101 A | 1/1988 | Gardner et al. |
| 4,856,496 A | 8/1989 | Chursinoff |
| 5,176,624 A | 1/1993 | Huehnreich |
| 5,357,696 A | 10/1994 | Gray et al. |
| 5,407,418 A | 4/1995 | Szpur |
| 5,443,440 A | 8/1995 | Tumey et al. |
| 5,584,798 A | 12/1996 | Fox |
| 5,605,533 A | 2/1997 | Badilla |
| 5,674,262 A | 10/1997 | Tumey et al. |
| 5,682,690 A | 11/1997 | Chang |
| 5,688,225 A | 11/1997 | Walker |
| 5,931,797 A | 8/1999 | Tumey et al. |
| 6,135,116 A | 10/2000 | Vogel et al. |
| 6,205,618 B1 | 3/2001 | Lee |
| 6,234,987 B1 | 5/2001 | Chen |
| 6,319,215 B1 | 11/2001 | Manor et al. |
| 6,360,457 B1 | 3/2002 | Qui et al. |
| 6,585,669 B2 | 7/2003 | Manor et al. |
| 6,615,080 B1* | 9/2003 | Unsworth ............ A61N 1/0452 607/2 |
| 6,685,661 B2 | 2/2004 | Peled |
| 6,702,768 B2 | 3/2004 | Mano et al. |
| 6,893,409 B1 | 5/2005 | Lina |
| 7,107,706 B1 | 9/2006 | Bailey, Sr. et al. |
| 7,188,439 B2 | 3/2007 | DiBenedetto et al. |
| 7,219,449 B1 | 5/2007 | Hoffberg et al. |
| 7,282,038 B2 | 10/2007 | Gillis et al. |
| 7,310,895 B2 | 12/2007 | Whittlesey et al. |
| 7,318,291 B2 | 1/2008 | Wang et al. |
| 7,395,614 B1 | 7/2008 | Bailey, Sr. et al. |
| 7,506,460 B2 | 3/2009 | DiBenedetto et al. |
| 7,544,173 B2 | 6/2009 | Suzuki |
| 7,596,891 B2 | 10/2009 | Carnes et al. |
| 7,607,243 B2 | 10/2009 | Berner, Jr. et al. |
| 7,618,382 B2 | 11/2009 | Vogel et al. |
| 7,631,382 B2 | 12/2009 | DiBenedetto et al. |
| 7,676,960 B2 | 3/2010 | DiBenedetto et al. |
| 7,909,783 B2 | 3/2011 | Mayer et al. |
| 7,980,009 B2 | 7/2011 | Carnes et al. |
| 8,056,268 B2 | 11/2011 | DiBenedetto et al. |
| 8,246,556 B2 | 8/2012 | Mayer et al. |
| 8,308,665 B2 | 11/2012 | Harry et al. |
| 9,283,139 B2 | 3/2016 | Mayer et al. |
| 2002/0068884 A1 | 6/2002 | Alviso |
| 2002/0133106 A1 | 9/2002 | Peled |
| 2003/0139255 A1 | 7/2003 | Lina |
| 2004/0030270 A1* | 2/2004 | Johnson ............ A61N 1/0452 601/15 |
| 2004/0059386 A1* | 3/2004 | Yu ............ A61N 1/32 607/2 |
| 2004/0064974 A1 | 4/2004 | Schuster |
| 2005/0126049 A1 | 6/2005 | Koenig |
| 2005/0187496 A1 | 8/2005 | Ho |
| 2005/0187601 A1* | 8/2005 | Wang ............ A61H 39/04 607/144 |
| 2006/0213091 A1 | 9/2006 | Ometto et al. |
| 2008/0010851 A1 | 1/2008 | Avanzini |
| 2008/0066343 A1 | 3/2008 | Sanabria-Hernandez |
| 2008/0071202 A1 | 3/2008 | Nardi et al. |
| 2008/0072451 A1 | 3/2008 | Mizrahi |
| 2008/0161734 A1 | 7/2008 | Blockton |
| 2009/0030354 A1 | 1/2009 | Ghatge |
| 2009/0069865 A1* | 3/2009 | Lasko ............ A61B 5/1038 607/49 |
| 2009/0149899 A1 | 6/2009 | Ahn |
| 2010/0010398 A1* | 1/2010 | Mayer ............ A61H 23/02 601/27 |
| 2010/0094184 A1 | 4/2010 | Wong et al. |
| 2011/0089725 A1 | 4/2011 | Shantha et al. |
| 2011/0166480 A1 | 7/2011 | Mayer |
| 2013/0041298 A1 | 2/2013 | Mayer et al. |

FOREIGN PATENT DOCUMENTS

| | | |
|---|---|---|
| CN | 1486148 | 3/2004 |
| CN | 2902266 | 5/2007 |
| EP | 1509101 | 3/2005 |
| JP | 2002325819 | 11/2002 |
| JP | 2004-526477 | 9/2004 |
| JP | 2006521879 | 9/2006 |
| JP | 2008114048 | 5/2008 |
| KR | 20-0265394 | 2/2002 |
| KR | 20030059973 | 7/2003 |
| KR | 20070049008 | 5/2007 |
| KR | 20080070175 | 7/2008 |
| WO | 95-10257 | 4/1995 |
| WO | 2005013743 | 2/2005 |
| WO | 2009152544 | 12/2009 |
| WO | WO 2011109725 | 9/2011 |

OTHER PUBLICATIONS

Non-Final Office Action dated Aug. 1, 2014 for U.S. Appl. No. 13/193,446.
Office Action dated Sep. 8, 2012 for Mexican Patent Application No. Mx/a/2011/000246.
Final Office Action dated Mar. 12, 2014 for U.S. Appl. No. 13/040,982.
Examination Report dated Feb. 9, 2015 for European Patent Application No. 09795105.7.
Examiner's Interview dated Mar. 20, 2012 for U.S. Appl. No. 13/004,754.
Examination Report dated Mar. 26, 2015 for Australian Patent Application No. 200926641.
Final Office Action dated Mar. 26, 2015 for U.S. Appl. No. 13/193,446.
Notice of Allowance dated Aug. 28, 2013 for Mexican Patent Application No. MX/a/2011/000246.
Restriction Requirement dated May 19, 2015 for U.S. Appl. No. 13/554,834.
Preliminary Report on Patentability dated Jun. 12, 2014 for PCT/US2012/067365.
Australian Patent Examination Report No. 1 dated May 13, 2014 for 2009268641.
European Search Report and Opinion dated Jun. 15, 2015 for European Patent Application No. 12853699.2.
Advisory Action dated Aug. 10, 2015 for U.S. Appl. No. 13/193,446.
Office Action dated Jul. 24, 2014 for Chinese Patent Application No. 200980132527.7.
Examination Report dated Aug. 5, 2014 for European Patent Application No. 09795105.7.

(56) References Cited

OTHER PUBLICATIONS

Office Action dated Aug. 28, 2015 for Canadian Patent Application No. 2730238.
Examination Report dated Nov. 6, 2015 for Australian Patent Application No. 2009268641.
Examination Report dated Sep. 8, 2015 for European Patent Application No. 09795105.7.
Non-Final Office Action dated Sep. 10, 2015 for U.S. Appl. No. 13/554,834.
Office Action dated Aug. 25, 2015 for Chinese Patent Application No. 201280068673.X.
Examination Report dated Aug. 19, 2015 for Australian Patent Application No. 2009268641.
European Search Report dated May 3, 2012 for PCT/US2009049910.
Office Action dated Jun. 9, 2013 in Chinese Patent Application No. 200980132527.7.
Office Action dated Mar. 6, 2014 for patent application in China application No. 200980132527.7.
International Preliminary Report on Patentability dated Feb. 27, 2014 for PCT/US2012/050290.
Office Action dated Aug. 3, 2012 for Mexican Patent Application No. MX/a/2011/000246.
International Preliminary Report on Patentability dated Sep. 20, 2012 for PCT/US2011/027220.
International Search Report dated Oct. 26, 2012 re: PCT/US2012/050290.
International Search Report and Written Opinion for PCT/US12/67365 dated Feb. 15, 2013.
Office Action dated Feb. 12, 2013 for Mexican Patent Application No. MX/a/2011/000246.
Office Action dated Mar. 5, 2013 for European Patent Application No. 09795105.7-1658.
Office Action dated May 15, 2013 for U.S. Appl. No. 13/040,982.
International Search Report dated Nov. 15, 2011 for PCT/US2009/049910.
International Search Report dated Nov. 22, 2011 for PCT/US2011/027220.
Non-Final Office Action dated Sep. 21, 2011 for U.S. Appl. No. 13/004,754.
Office Action dated May 2, 2012 for MX/a/2011/000246.
Office Action dated Feb. 7, 2012 for U.S. Appl. No. 13/004,754.
Notice of Allowance dated Dec. 15, 2010 for U.S. Appl. No. 12/499,473.
Notice of Allowance dated Nov. 29, 2010 for U.S. Appl. No. 12/499,473.
Final Office Action dated Jun. 22, 2010 for U.S. Appl. No. 12/499,473.
Non-Final Office Action dated Apr. 15, 2010 for U.S. Appl. No. 12/499,473.
Office Action dated Jan. 8, 2016 for Korean Patent Application No. 2011-7001073.
Notice of Allowance dated Dec. 7, 2015 for U.S. Appl. No. 13/193,446.
Final Office Action dated Jan. 13, 2016 for U.S. Appl. No. 13/554,834.
Notice of Allowance and Examiner's Interview Summary dated May 3, 2016 for U.S. Appl. No. 13/554,834.
Office Action dated Mar. 10, 2016 for Chinese Patent Application No. 20150026309.2.
Office Action dated Mar. 24, 2016 for Korean Patent Application No. 2011-7001073.
Office Action dated Mar. 29, 2016 for Chinese Patent Application No. 201280068673.X.
Office Action dated Nov. 1, 2016 for Chinese Patent Application No. 20150026309.2.
U.S. Appl. No. 13/554,834, filed Jul. 20, 2012, Foot Compression System.
U.S. Appl. No. 13/040,982, filed Mar. 4, 2011, Therapy Shoe.
U.S. Appl. No. 14/362,108, filed May 30, 2014, Spring Driven Foot Compression System.
U.S. Appl. No. 14/637,143, filed Mar. 3, 2015, Insole Foot Compression System and Methods.
International Search Report and Written Opinion dated Jul. 29, 2016 for PCT/US2016/019236.
Office Action dated Jun. 10, 2016 for Canadian Patent Application No. 2,730,238.
Office Action dated Jun. 27, 2016 for Chinese Patent Application No. 201280068673.X.

* cited by examiner

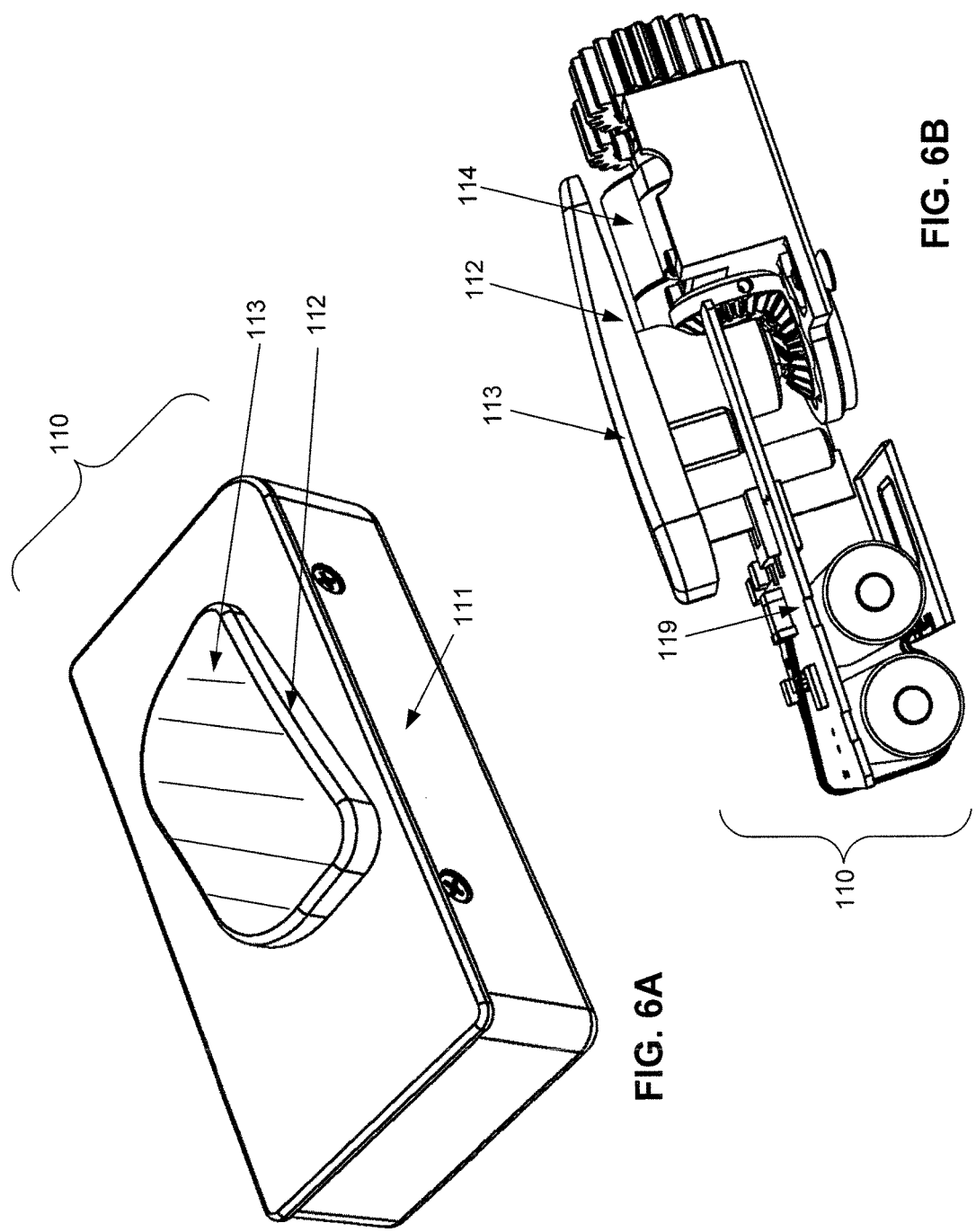

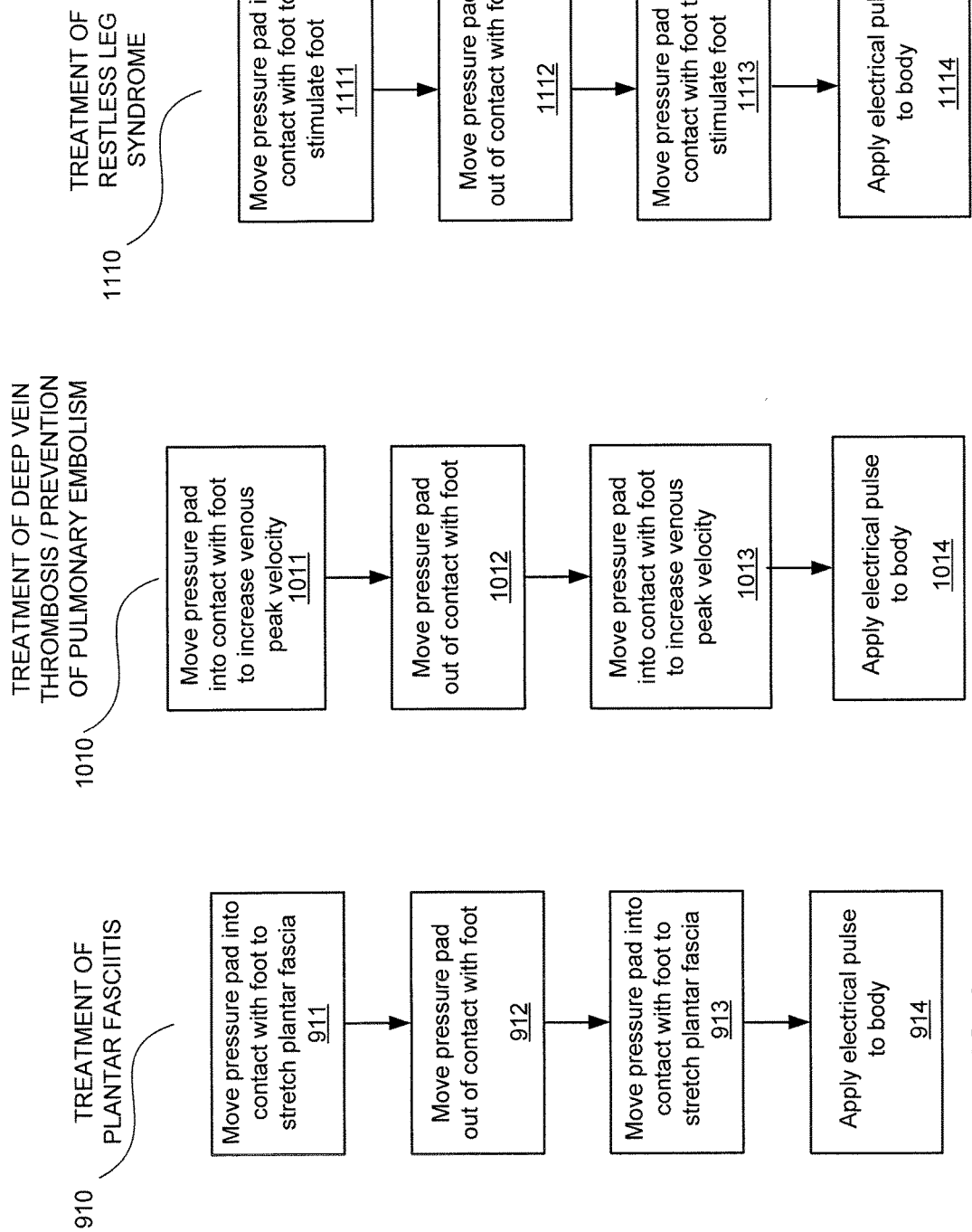

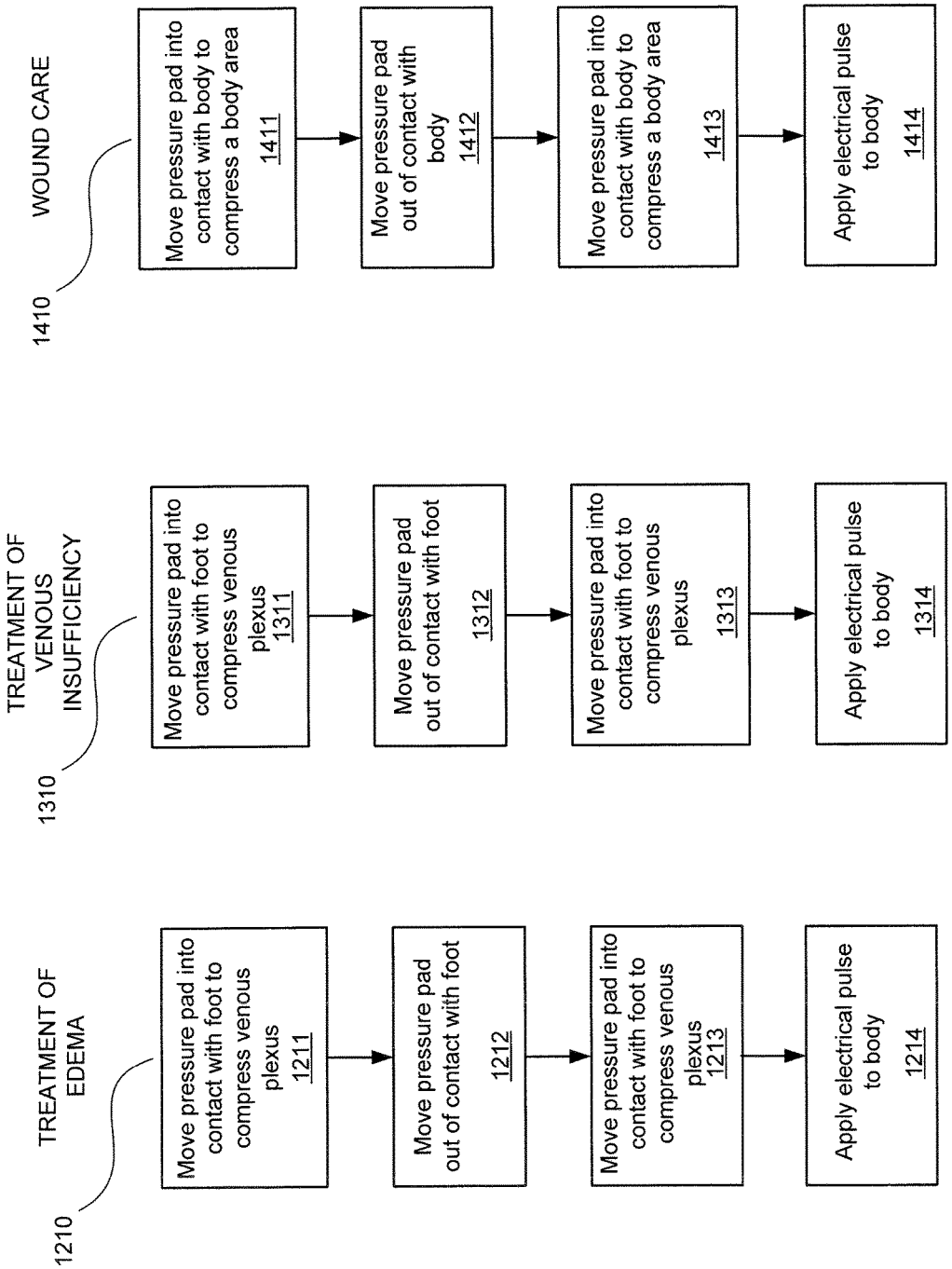

FOOT COMPRESSION AND ELECTRICAL STIMULATION SYSTEM

CROSS-REFERENCE TO RELATED APPLICATIONS

This application is a continuation of PCT Application No. PCT/US2012/050290 having an international filing date of Aug. 10, 2012 and entitled "FOOT COMPRESSION AND ELECTRICAL STIMULATION SYSTEM". PCT Application No. PCT/US2012/050290 claims priority to U.S. Provisional Application No. 61/523,023 filed on Aug. 12, 2011 and entitled "FOOT COMPRESSION AND ELECTRICAL STIMULATION SYSTEM". The entire contents of all the foregoing applications are hereby incorporated by reference.

TECHNICAL FIELD

The present disclosure generally relates to systems and methods for creating a similar amount of blood flow to a part of the body, such as the legs and feet, as would be experienced during muscle contraction and movement, such as walking. To this end, the present disclosure generally relates to systems and methods for mechanically compressing an area of the body, such as the venous plexus region in the arch of the foot, and the superficial veins of the top of the foot to stimulate blood flow, while electrically stimulating the muscles proximate to the same area and surrounding areas, such as the calf and thigh.

BACKGROUND

Under normal circumstances, blood moves up the legs due to muscle contraction and general movement of the feet or legs, such as when walking. If a person is immobilized, unable to move regularly, or has poor circulation brought on by disease, the natural blood return mechanism is impaired, and circulatory problems such as ulcers, deep vein thrombosis, and pulmonary embolisms can occur.

To mitigate the problems caused by low mobility and poor circulation, it is desirable to enhance circulation through alternative means that attempt to mimic the effects of walking. Ideally, a device to enhance circulation would create the same amount of blood flow to the lower extremities as one would obtain via walking. One exemplary device is a device set forth in U.S. Pat. No. 7,909,783. While this device significantly enhances circulation to stimulate the effects of walking, further enhancement of circulation to substantially replicate the effects of walking remains desirable.

SUMMARY

A compression and electrical stimulation system is configured to apply pressure to a foot and electrically stimulate the muscles of the same or surrounding areas (e.g., foot and leg) to contract, for example in order to increase circulation. In an exemplary embodiment, a system configured in accordance with principles of the present disclosure comprises an actuator portion comprising a retractable, non-bendable pressure pad and an electrical muscle stimulator that may optionally be combined with a compression garment. Another exemplary embodiment further comprises an item of footwear, wherein the actuator portion is completely contained within the item of footwear. Similarly, in other exemplary embodiments, the electrical muscle stimulator is completely contained within an item of footwear.

In various exemplary embodiments, a compression and stimulation system configured in accordance with principles of the present disclosure may be utilized for one or more of athletic warm-up or recovery, the removal of metabolic waste, wound care and recovery, or the treatment of medical conditions including plantar fasciitis, restless leg syndrome, deep vein thrombosis, pulmonary embolism, venous insufficiency, and/or the like.

BRIEF DESCRIPTION OF THE DRAWINGS

The subject matter of the present disclosure is particularly pointed out and distinctly claimed in the concluding portion of the specification. The present disclosure, however, both as to organization and method of operation, may best be understood by reference to the following description taken in conjunction with the claims and the accompanying drawing figures, in which like parts may be referred to by like numerals:

FIGS. 6A-6D illustrate a compression and stimulation system in accordance with an exemplary embodiment;

FIG. 9 illustrates the utilization of compression and stimulation system 100 in the treatment of plantar fasciitis;

FIG. 10 illustrates the utilization of compression and stimulation system 100 in the treatment of deep vein thrombosis and/or prevention of pulmonary embolism;

FIG. 11 illustrates the utilization of compression and stimulation system 100 in the treatment of restless leg syndrome;

FIG. 12 illustrates the utilization of compression and stimulation system 100 in the treatment of edema;

FIG. 13 illustrates the utilization of compression and stimulation system 100 in the treatment of venous insufficiency; and FIG. 14 illustrates the utilization of compression and stimulation system 100 in the treatment of wounds.

DETAILED DESCRIPTION

Details of the present disclosure may be described herein in terms of various components and processing steps. It should be appreciated that such components and steps may be realized by any number of hardware and/or software components configured to perform the specified functions.

For example, the system may employ various medical treatment devices, input and/or output elements and the like, which may carry out a variety of functions under the control of one or more control systems or other control devices. In addition, details of the present disclosure may be practiced in any number of medical or treatment contexts, and exemplary embodiments relating to a compression and stimulation system, for example usable in connection with treatment of deep vein thrombosis, or in connection with athletic recovery, as described herein are merely a few of the exemplary applications. For example, the principles, features and methods discussed may be applied to any medical or other tissue or treatment application.

Further, the principles of the present disclosure are described herein with continued reference to a foot for purposes of explanation. However, such principles may also be applied to other parts of a body, for example when an improvement of circulation is desired.

Significant health benefits can be achieved by the addition of electrical stimulation to a compression and stimulation system. For example, health benefits comparable to or equal to the benefits arising from walking may be achieved by combining a compression device with an electrical stimulation in accordance with principles of the present disclosure.

Figure 1:
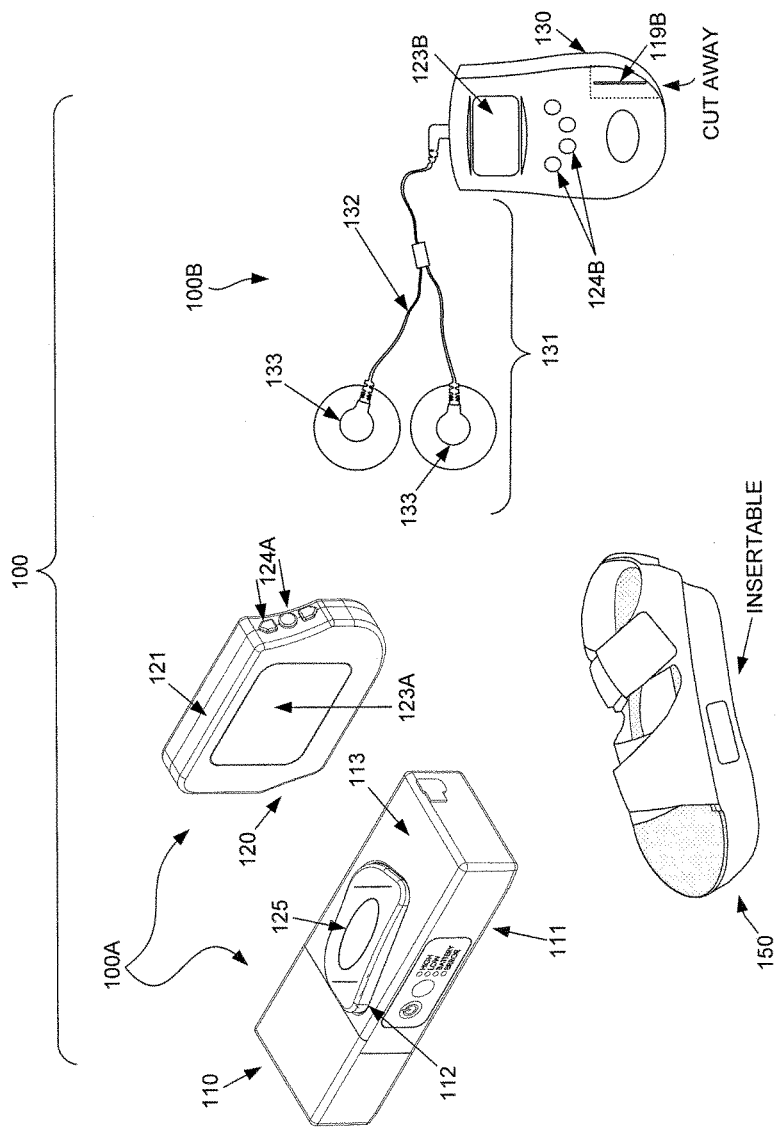
FIG. 1 illustrates a compression and stimulation system in accordance with an exemplary embodiment.

A foot compression and electrical stimulation system may be any system configured to deliver a reciprocating compressive force and electrical stimulation to a portion of a living organism, for example a human foot, calf, or thigh. With reference now to FIG. 1, and in accordance with an exemplary embodiment, compression and stimulation system 100 comprises a tissue depressor 100A and an electrical muscle stimulator 100B. Tissue depressor 100A is configured to deliver a reciprocating compressive force to a portion of a living organism, preferably a human foot. Electrical muscle stimulator 100B is configured to generate an electrical pulse to a portion of the living organism. In one exemplary embodiment, the electrical pulse is applied to the same or neighboring portions of the living organism as the portion receiving the compressive force delivered by tissue depressor 100A. Moreover, compression and stimulation system 100 may be configured with any appropriate components and/or elements configured to deliver a reciprocating compressive force and an electrical pulse to a portion of a living organism.

In an exemplary embodiment, tissue depressor 100A comprises an actuator portion 110. In an exemplary embodiment, electrical muscle stimulator 100B comprises a pulse generator 130 coupled to at least two electrodes 131 and control electronics 119B. In an exemplary embodiment, actuator portion 110 may be responsive to communication with one or more of a reader portion 120, a computer, or an input 124A.

With further reference now to FIGS. 2A-2B, 3, and 4A-4C, and in accordance with an exemplary embodiment, actuator portion 110 comprises depressor housing 111, pressure pad 112, pad top 113, motor 114, gearbox 115, output gears 116, main gears 117, slip clutch 118, control electronics 119A, and weight sensor 125. Reader portion 120 comprises control box 121, batteries 131A (not shown in figures), display 123, and inputs 124A. In an exemplary embodiment not comprising a reader portion, actuator portion 110 may further comprise inputs 124A. In various other exemplary embodiments, certain components are not present, for example slip clutch 118 and reader portion 120.

Actuator portion 110 may be any device, system, or structure configured to apply a compressive force to a foot. In an exemplary embodiment, actuator portion 110 is configured to be removably located in the sole area of an item of footwear 150 such as a shoe, sandal, or any other type of footwear product. In other exemplary embodiments, actuator portion 110 may be integrated into footwear 150. Actuator portion 110 may also be a stand-alone unit, for example a footrest.

In various exemplary embodiments, actuator portion 110 has an outer shape at least partially defined by a depressor housing 111. Depressor housing 111 may be formed of metal, plastic, composite, or other suitable durable material. Depressor housing 111 is configured to enclose various portions of tissue depressor 100A. Depressor housing 111 may also be configured to house various portions of the electrical muscle stimulator 100B along with portions of the tissue depressor 100A. Actuator portion 110 may be configured to be entirely contained within and/or integrated into an item of footwear, for example, a shoe.

Figure 2A:
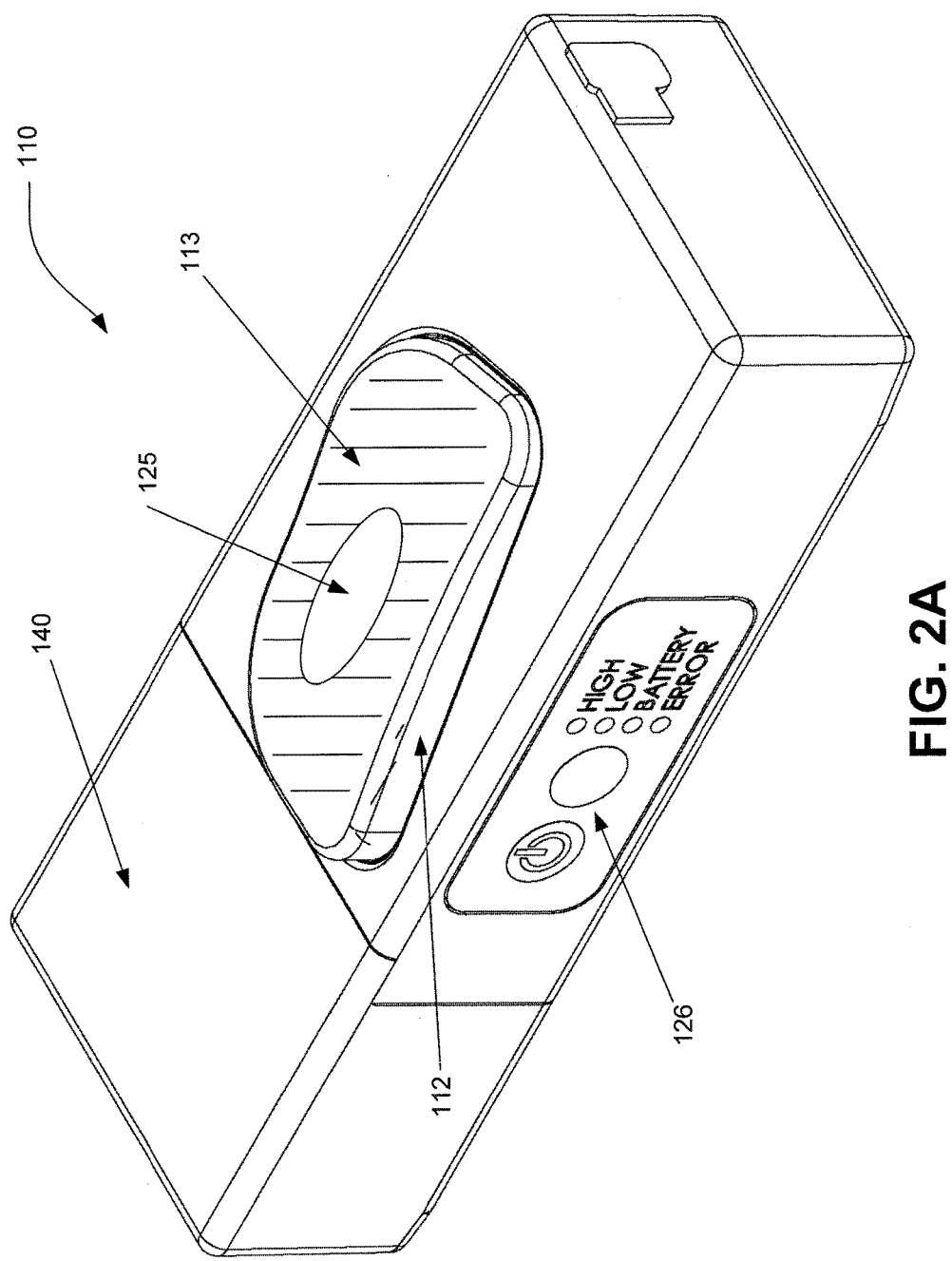
FIG. 2A illustrates an actuator portion of a compression and stimulation system in accordance with an exemplary embodiment.
Figure 2B:
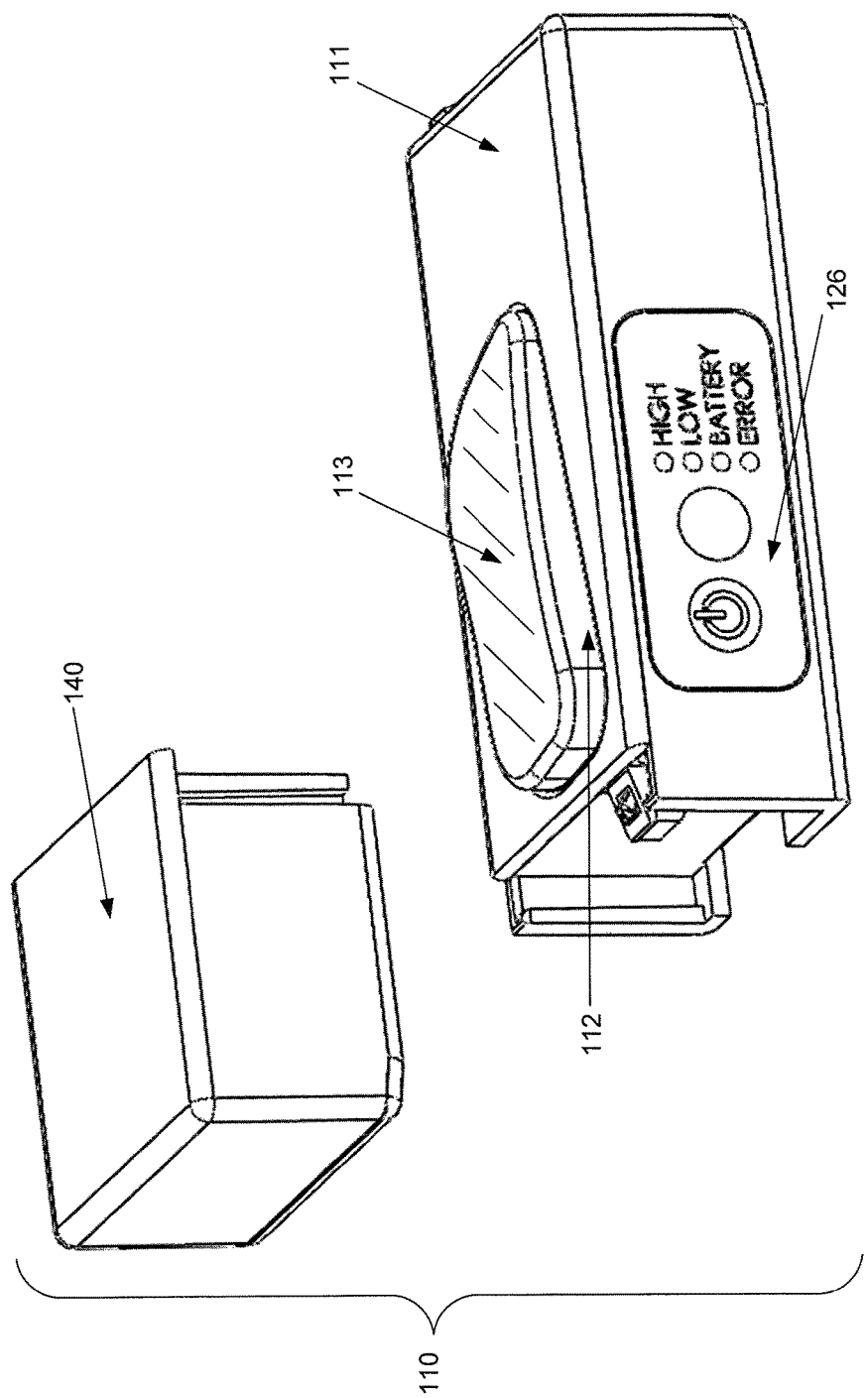
FIG. 2B illustrates an actuator portion of a compression and stimulation system with a battery detached in accordance with an exemplary embodiment.
Figure 3:
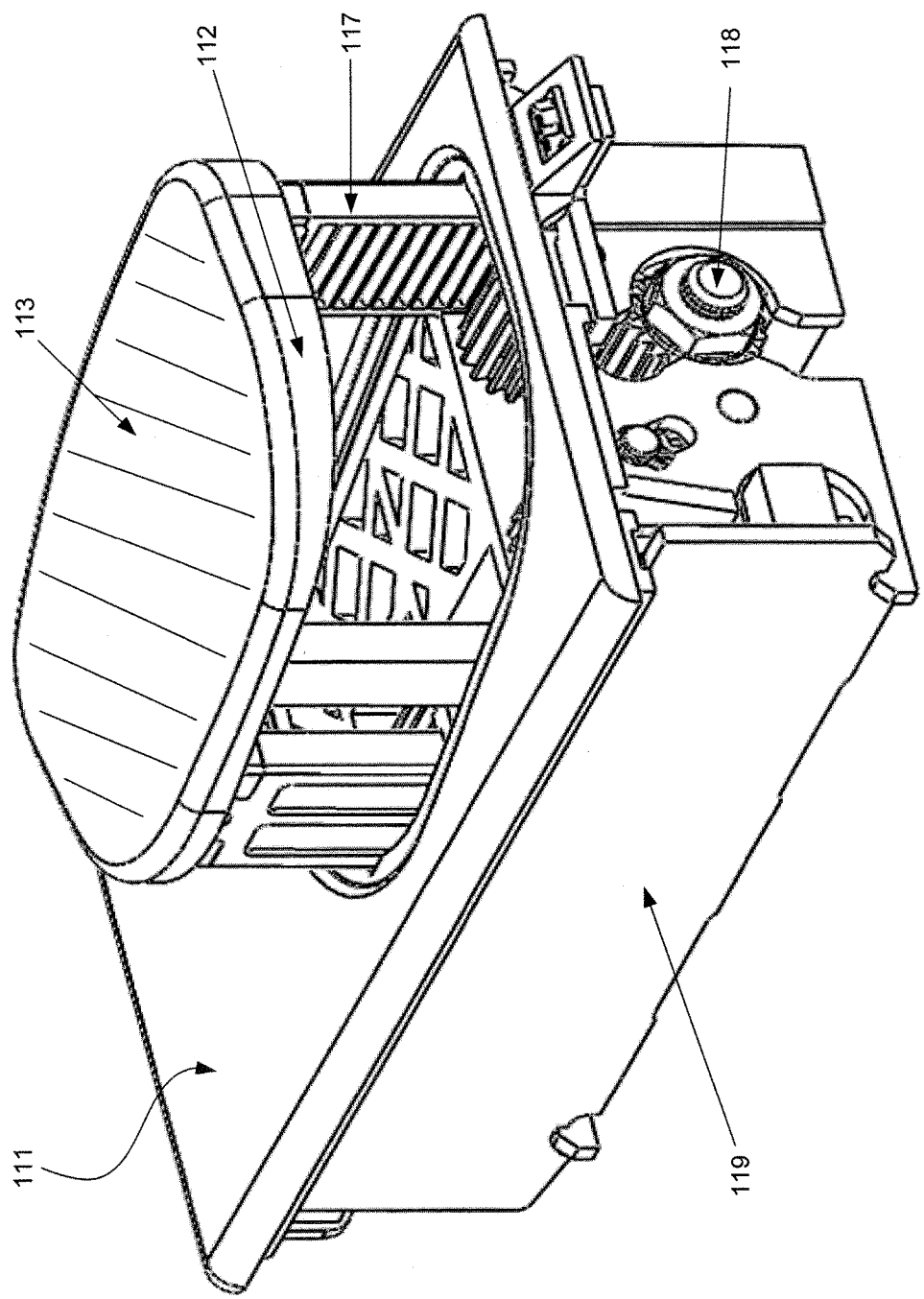
FIG. 3 illustrates various components of an actuator portion of a compression and stimulation system in accordance with an exemplary embodiment.

Turning now to FIGS. 2A through 3, and in accordance with an exemplary embodiment, pressure pad 112 comprises a rigid or semi-rigid structure configured to press against a person's foot. In various exemplary embodiments, pressure pad 112 is extendable and retractable. Moreover, pressure pad 112 may be rigid, semi-rigid, non-deformable, and/or non-bendable. Pressure pad 112 is coupled to main gears 117. Moreover, pressure pad 112 may be configured to be moved by and/or coupled to any suitable power transfer components.

Pressure pad 112 may be made of any suitable materials, for example metal, plastic, composite, and/or the like. Moreover, pressure pad 112 may be comprised of any material suitable for transferring force to a person's foot. Pressure pad 112 may also be monolithic. Alternatively, pressure pad 112 may comprise two or more individual components. In certain exemplary embodiments, pressure pad 112 comprises a rigid main structure configured with a flexible pad top 113, for example a pad top 113 comprised of rubber, silicone, or other suitable material. Pad top 113 may be smooth, ridged, dimpled, patterned, and/or otherwise shaped and/or textured. In this manner, pressure pad 112 may be configured to press against a person's foot while providing a desired level of cushioning, comfort, friction, and/or the like, for example due to pad top 113.

Pressure pad 112 can be any size to transfer a desired amount of force to a person's foot. According to an exemplary embodiment, pressure pad 112 applies force directly to the arch region of the foot. In various exemplary embodiments, pressure pad 112 comprises a contact surface area in the range of about 6 square centimeters to about 30 square centimeters. In various exemplary embodiments, pressure pad 112 comprises a contact surface area in the range of about 10 square centimeters to about 24 square centimeters. In other exemplary embodiments, pressure pad 112 comprises a contact surface area in the range of about 18 square centimeters to about 23 square centimeters. However, pressure pad 112 may be configured with any appropriate dimensions, surfaces, angles, and/or components, as desired, in order to transfer force to a foot. For example, in certain exemplary embodiments wherein compression and stimulation system 100 is utilized in connection with athletic recovery, pressure pad 112 may be configured with a contact surface area substantially equal to the surface area of the bottom of a foot, for example a contact surface area in the range of between about 100 square centimeters to about 150 square centimeters.

In various exemplary embodiments, pressure pad 112 further comprises a pressure sensor 125 configured to measure the pressure generated by pressure pad 112. The pressure sensor may communicate with control electronics 119A and/or other components of compression and stimulation system 100 in order to achieve a desired level of pressure generated by pressure pad 112.

In accordance with an exemplary embodiment, pressure pad 112 may be kept in an extended position for a time between about 1 and 5 seconds. In various exemplary embodiments, pressure pad 112 is pressed against the venous plexus region of the foot for a time between approximately 1 and 5 seconds, and preferably closer to 2 seconds. When extended away from depressor housing 111, pressure pad 112 presses against the venous plexus region of the foot. Pressure pad 112 compresses the veins both in the arch of the foot and across the top of the foot from approximately the metatarsal-phalangeal joints to the talus. However, principles of the present disclosure contemplate pressure pad 112 pressing against any desired site on a body and being kept in an extended position for any suitable time, for example to stimulate blood flow.

In an exemplary embodiment, pressure pad 112 is configured to extend and/or retract over a desired time period. In various exemplary embodiments, pressure pad 112 is configured to extend from a fully retracted position to a fully extended position in a time between about 0.1 second and about 1 second, and preferably between about 0.1 second and about 0.3 seconds. However, pressure pad 112 may be configured to extend and/or retract over any suitable time period. Moreover, variances in between individuals (e.g., the unique features of a foot such as height of arch, curvature of arch, width, length, and/or the like) may effect the time period over which pressure pad is deployed.

In an exemplary embodiment, pressure pad 112 retracts so that it is flush or nearly flush with an outer surface of depressor housing 111. Compression and relaxation is then followed by a period of non-compression to allow the veins to re-fill with blood. In various exemplary embodiments, pressure pad 112 is pressed against the venous plexus region of the foot and then retracted in regular intervals of between about 20 seconds to about 45 seconds, and preferably between 25 seconds to 35 seconds. However, pressure pad 112 may be pressed against the venous plexus region of the foot and then retracted in any suitable interval, for example to stimulate blood flow. For example, compression may be rapid in order to move blood through the veins of the lower leg at an elevated velocity and to release chemical compounds that reduce pain.

In various exemplary embodiments, switches may be employed to ensure that pressure pad 112 does not extend beyond a pressure threshold, such as between about 1 mmHg and 500 mmHg, and more preferably between about 300 mmHg and about 465 mmHg. In various exemplary embodiments, pressure pad 112 is extended with a force of between about 50 Newtons and about 115 Newtons, and more preferably between about 60 Newtons and about 100 Newtons. While various pressures and/or forces have been described herein, other pressures and/or forces can be applied and fall within the scope of the present disclosure. Moreover, switches and/or other devices may be placed at the locations of maximum and/or minimum extension of pressure pad 112 in order to ensure that motor 114 is appropriately shut off at the end of travel.

While specific time ranges, sizes, pressures, movement distances, and the like have been described herein, these values are given purely for example. Various other time ranges, sizes, pressures, distances, and the like can be used and fall within the scope of the present disclosure. Any device configured to apply pressure to a person's foot as set forth herein is considered to fall within the scope of the present disclosure.

In accordance with an exemplary embodiment, switches and/or other appropriate mechanisms may be located at the maximum and/or minimum extensions of pressure pad 112 in order to prevent motor 114 from attempting to force pressure pad 112 beyond the end of travel. Such switches or other travel-limiting devices may be implemented mechanically, in hardware, in software, or any combination of the foregoing.

Figure 4A:
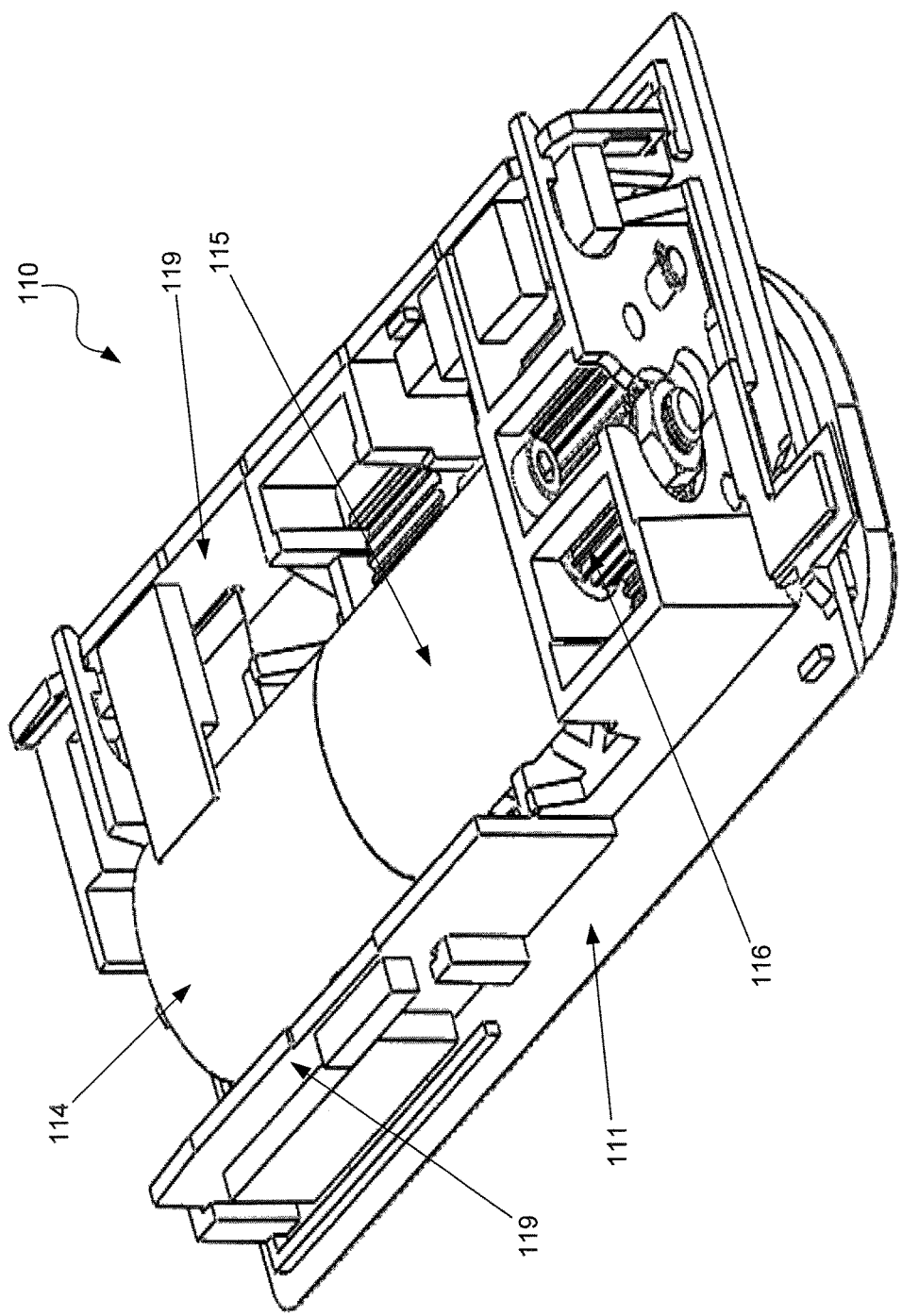
FIGS. 4A through 4C illustrate various components of an actuator portion of a compression and stimulation system in accordance with an exemplary embodiment.
Figure 4B:
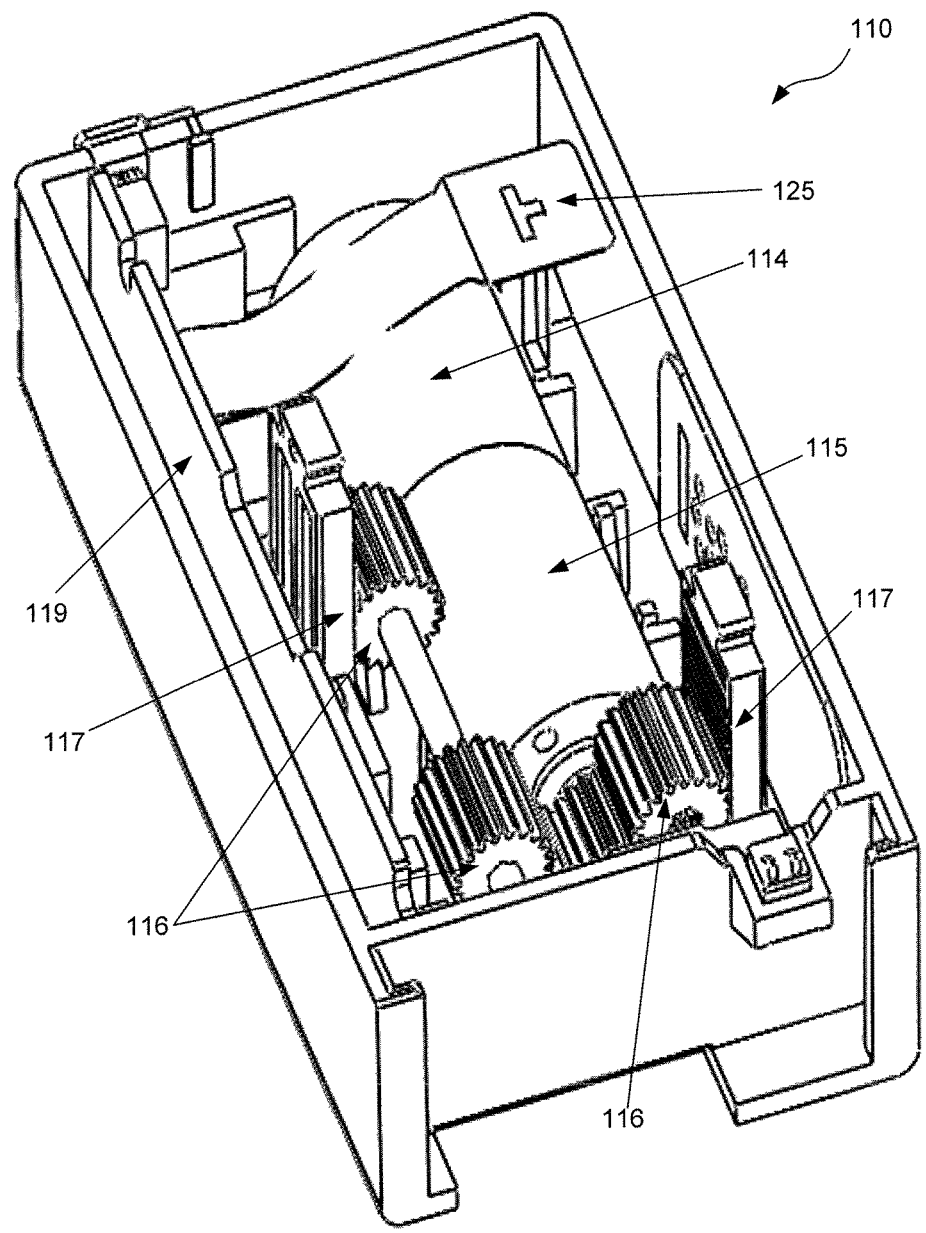
Figure 4C:
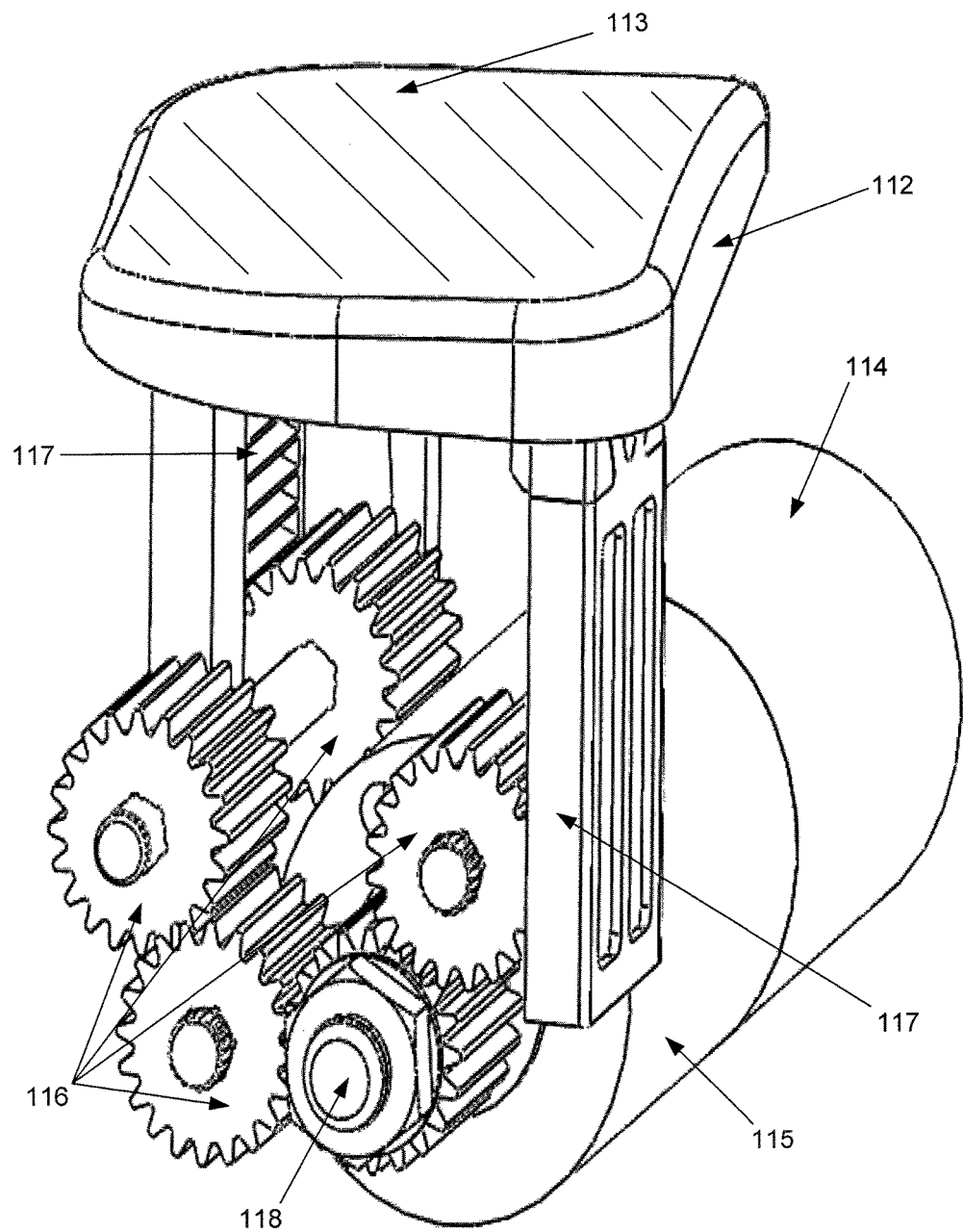

Motor 114 may be any component configured to generate mechanical force to move pressure pad 112. With reference now to FIGS. 4A through 4C, and in accordance with an exemplary embodiment, motor 114 comprises a rotary output shaft driving a pinion. Motor 114 may comprise any suitable motor, such as a brushless direct current (DC) motor, a brushed DC motor, a coreless DC motor, a linear DC motor, and/or the like. Moreover, any motor, actuator, micro-engine, or similar device presently known or adopted in the future to drive moving parts within actuator portion 110 falls within the scope of the present disclosure. In various other exemplary embodiments, motor 114 may be replaced with another suitable power generation mechanism capable of moving pressure pad 112, such as an artificial muscle, a piezoelectric material, a shape memory alloy, and/or the like. Motor 114 is coupled to gearbox 115.

With continued reference to FIGS. 4A through 4C, and in accordance with an exemplary embodiment, gearbox 115 comprises a mechanism configured to increase the mechanical advantage obtained by motor 114, for example a reduction gearbox. Gearbox 115 is coupled to motor 114 and to output gears 116. Output force from motor 114 is transferred through gearbox 115 in order to achieve an appropriate gear ratio for effectuating movement of pressure pad 112. Thus, gearbox 115 may have a fixed gear ratio. Alternatively, gearbox 115 may have a variable or adjustable gear ratio. Gearbox 115 may comprise any suitable ratio configured in any suitable matter to effectuate movement of pressure pad 112. Moreover, gearbox 115 may comprise any suitable components, configurations, ratios, mechanisms, and/or the like, as desired, in order to transfer output force from motor 114 to other components of actuator portion 110, for example output gears 116

Output gears 116 may comprise any mechanism configured to transfer force from gearbox 115 to main gears 117. Continuing to reference FIGS. 4A through 4C, in accordance with an exemplary embodiment, output gears 116 comprise metal, plastic, or other durable material. Output gears 116 are coupled to gearbox 115 and to main gears 117. Output force from motor 114 is transferred through gearbox 115 to output gears 116. Output gears 116 are further configured to interface with main gears 117. Moreover, output gears 116 may comprise any composition or configuration suitable to transfer force to main gear 112.

Main gears 117 may comprise any suitable component or structure configured to effectuate movement of pressure pad 112. As illustrated in FIGS. 4A through 4C, in an exemplary embodiment, one or more main gears 117 are coupled to pressure pad 112. Main gears 117 interface with output gear 110. As main gears 117 move in response to force transferred by output gears 116, pressure pad 112 is extended and/or retracted through its range of motion. In various exemplary embodiments, main gears 117 are configured to effectuate movement of pressure pad 112 a distance of between about 1 mm to about 24 mm from a fully retracted to a fully extended position. In various other exemplary embodiments, main gears 117 are configured to effectuate movement of pressure pad 112 a distance of between about 12 mm to about 24 mm from a fully retracted to a fully extended position. Moreover, movement of pressure pad 112 may vary based on an individual user. For example, pressure pad 112 may be extended a larger distance for a user having a higher foot arch, and a smaller distance for a user having a lower foot arch. Additionally, pressure pad 112 may be moved between a fully retracted and a partially extended position, for example if a desired pressure value is reached via partial extension of pressure pad 112. Pressure pad 112 may also move responsive to operation of slip clutch 118.

With reference to FIGS. 4A through 4C, slip clutch 118 may comprise any mechanism configured to prevent damage to motor 114 and/or injury to a person. For example, if a person applies excessive force or weight to their foot when pressure pad 112 is extended, slip clutch 118 allows pressure pad 112 to safely retract back towards depressor housing 111. In an exemplary embodiment, slip clutch 118 is a friction clutch. Slip clutch 116 is configured to slip when excessive force is placed on pressure pad 112. In various exemplary embodiments, slip clutch 118 is configured to slip when the force on pressure pad 112 exceeds between about 130 Newtons to about 200 Newtons. In another exemplary embodiment, slip clutch 118 is configured to slip when the force on pressure pad 112 exceeds 155 Newtons. Moreover, slip clutch 118 may be configured to slip responsive to any suitable force in order to prevent damage to motor 114 or other components of actuator portion 110 and/or injury to a person.

With reference now to FIGS. 2A and 2B, in an exemplary embodiment, compression and stimulation system 100 may further comprise one or more indicators 126. Indicators 126 may be locatable on actuator portion 110, reader portion 120, and/or pulse generator 130. Indicators 126 may comprise any components configured to receive input from a user and/or to deliver feedback to a user. For example, indicators 126 may comprise on/off buttons, lights, switches, and/or the like. In an exemplary embodiment, indicators 126 comprise a power button, a "high" foot compression setting light, a "low" foot compression setting light, a battery level warning light, and an error message light. Moreover, indicators 126 may comprise any suitable input and/or output components, as desired.

With reference to FIG. 4B, in accordance with an exemplary embodiment, weight sensor 125 is provided within depressor housing 111. Weight sensor 120 comprises any suitable sensor configured to detect weight applied to depressor housing 111. When weight sensor 125 detects a suitable amount of weight, such as 25 pounds or more, control electronics 119A may infer that the person is walking or otherwise putting pressure on actuator portion 110. Moreover, any appropriate weight may be utilized, and thus falls within the scope of the present disclosure. Accordingly, control electronics 119A, 119B may implement a delay in activating compression and stimulation system 100 to ensure pressure pad 112 is not extended or pulse generator 130 does not generate a pulse.

In various exemplary embodiments, compression and stimulation system 100 may comprise various sensors, for example pressure sensors, weight sensors, strain gauges, accelerometers, motion sensors and/or the like. In one embodiment, actuator portion 110 and/or reader portion 120 may utilize one or more sensors for monitoring and/or control of compression and stimulation system 100. For example, in certain exemplary embodiments it may be desirable to prevent extension of pressure pad 112 or the generation of an electrical pulse when a person is walking or applying body weight to actuator portion 110. Thus, control electronics 119A, 119B may prevent extension of pressure pad 112 or generation of an electrical pulse, for example, in response to sensor input indicating a person is walking (e.g., accelerometer readings, weight sensor readings, motion sensor readings, and/or the like).

In various exemplary embodiments, compression and stimulation system 100 may be configured to be turned "on" when a user is seated and/or recumbent, and configured to be turned to a "standby" mode when a user is standing and/or walking. In an exemplary embodiment, control electronics 119A, 119B may prevent operation of compression and stimulation system 100 unless the sensor reports to control electronics 119A, 119B that the person utilizing compression and stimulation system 100 has been seated or otherwise stationary or recumbent for a suitable period of time, e.g. between 2 and 10 minutes.

Figure 5:
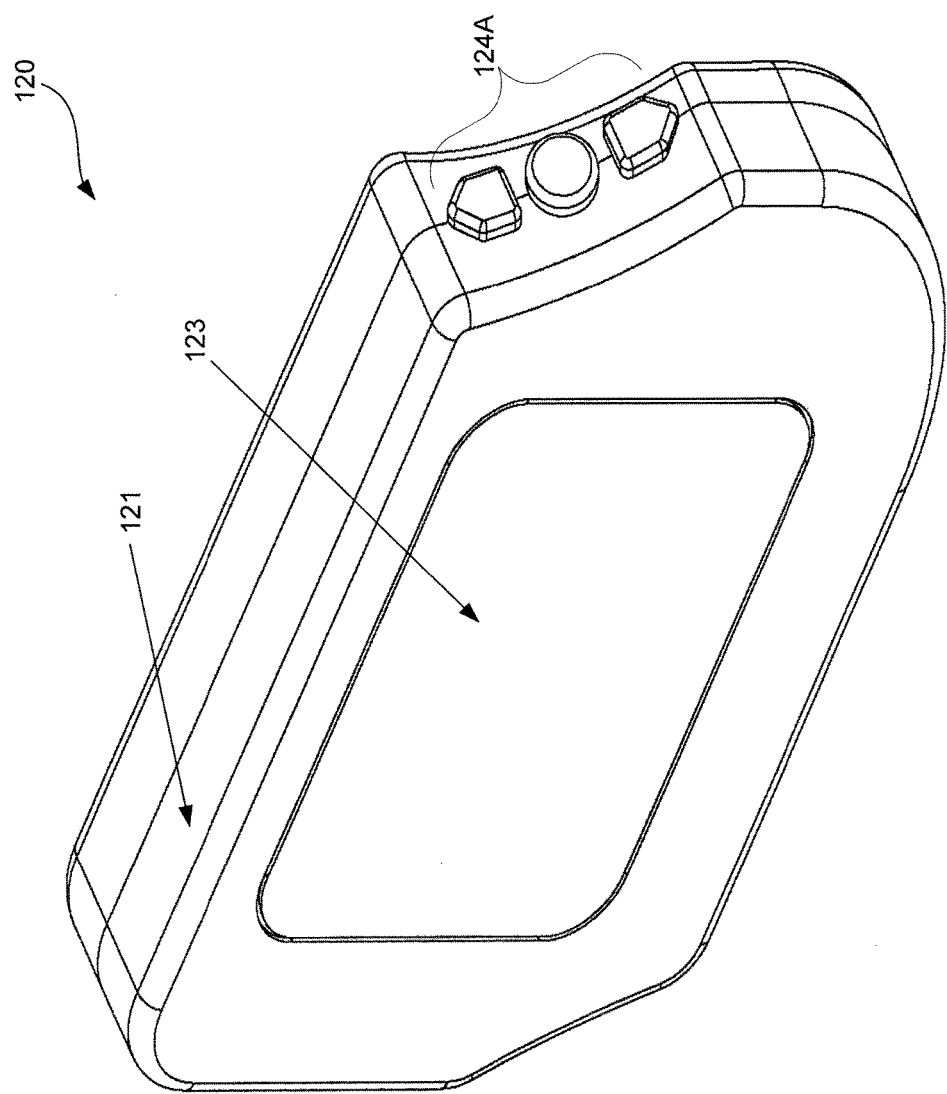
FIG. 5 illustrates a reader portion of a compression and stimulation system in accordance with an exemplary embodiment.
Figure 6C:
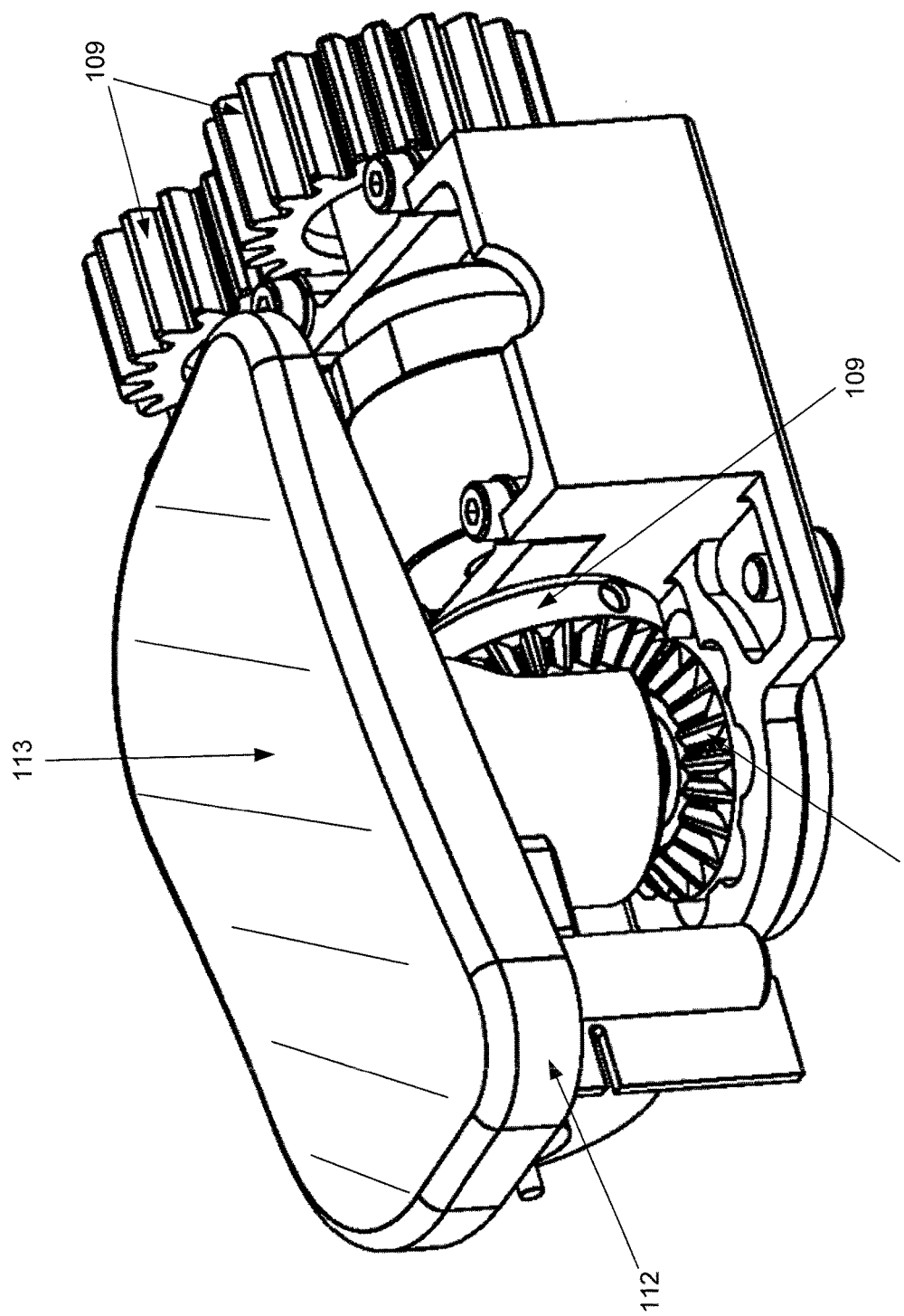
Figure 6D:
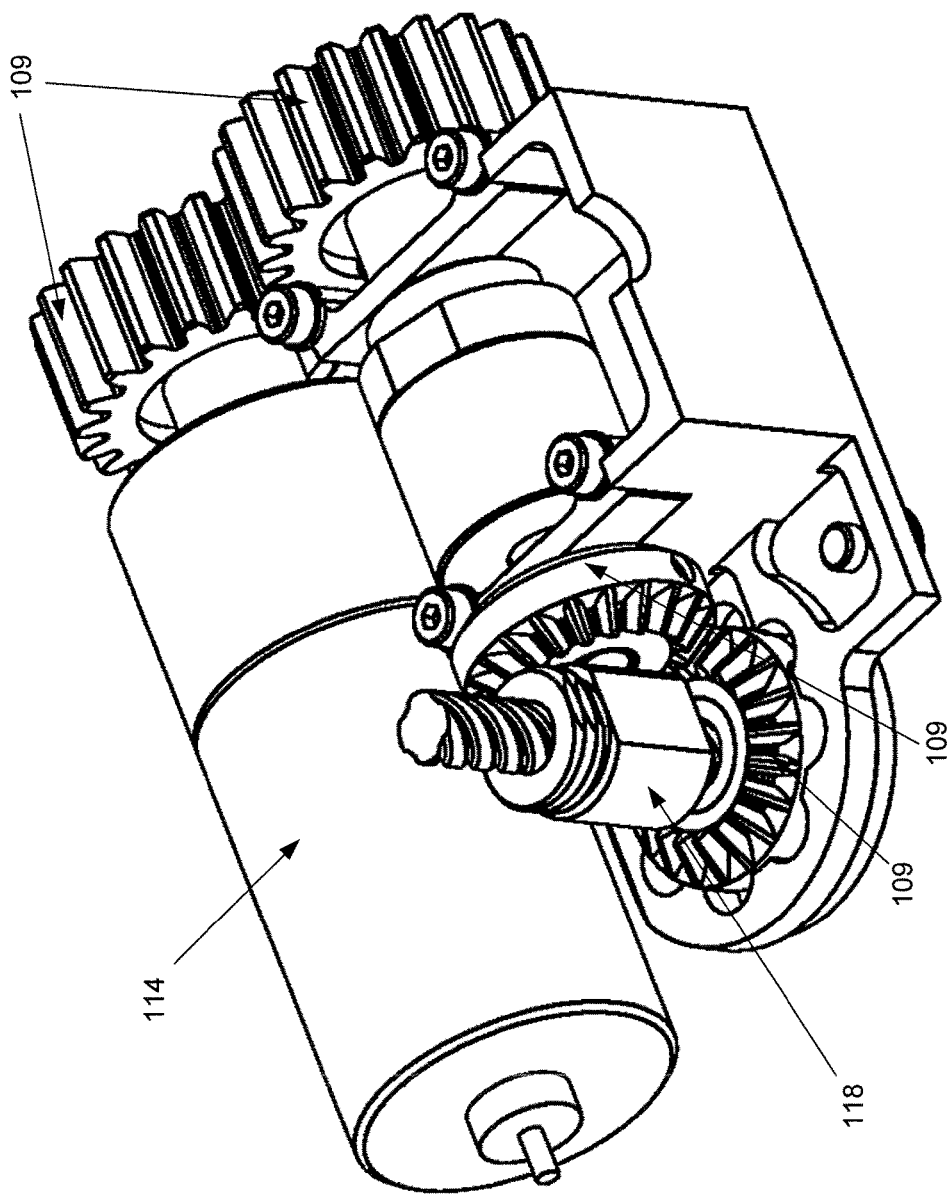

With reference now to FIGS. 1 and 5, and in accordance with an exemplary embodiment, tissue depressor 100A comprises a reader portion 120 configured to facilitate communication with and/or control other components of compression and stimulation system 100. such as actuator portion 110 and/or electrical muscle stimulator 100B. Reader portion 120 may comprise any suitable components, circuitry, displays, indicators, and/or the like, as desired. For example, reader portion 120 may be configured with a control box 121 comprising metal, plastic, composite, or other durable material suitable to contain various components of reader portion 120. In an exemplary embodiment, reader portion 120 is coupled to actuator portion 110 or electrical muscle stimulator 100B via a cable, for example an electrical cable suitable to carry current to drive motor 114, carry digital signals, carry analog signals, and/or the like. In other exemplary embodiments, reader portion 120 communicates wirelessly with other components actuator portion 110 or electrical muscle stimulator 100B, for example via a suitable communication protocol (e.g., IEEE 802.15.4; IEEE 802.15.1-2002 and/or IEEE 802.15.1-2005 (Bluetooth™); IEEE 802.11, IEEE 1451, ISA 100.11a; and/or the like). In these exemplary embodiments, reader portion 120 and the other components of compression and stimulation system 100 in communication with reader portion 120 may further comprise transceivers, receivers, transmitters and/or similar wireless technology.

With reference now to FIG. 5, and in accordance with an exemplary embodiment, reader portion 120 further comprises a display 123 configured for presenting information to a user. In an exemplary embodiment, display 123 comprises a liquid crystal display (LCD). In other exemplary embodiments, display 123 comprises light emitting diodes (LEDs). In still other exemplary embodiments, display 123 comprises visual and audio communication devices such as speakers, alarms, and/or other similar monitoring and/or feedback components. Moreover, display 123 may also comprise audible or tactile feedback components. Display 123 is configured to provide feedback, for example to a user of compression and stimulation system 100, or a medical practitioner. Moreover, display 123 may comprise any suitable components configured to provide information to a user of compression and stimulation system 100 or a medical practitioner. In accordance with exemplary embodiments, reader portion 120 may also comprise one or more batteries 122 (not shown in figures) as described herein.

With continued reference to FIG. 5, inputs 124A and/or 124B (collectively, "inputs 124") may comprise any components configured to allow a user to control operation of compression and stimulation system 100. In an exemplary embodiment, inputs 124 allow a user to turn compression and stimulation system 100 on and off. Inputs 124 may also allow a user to adjust operating parameters of both the tissue depressor 100A and the electrical muscle stimulator 100B. Parameters for tissue depressor 100A may include, for example, the interval of extension of pressure pad 112, the force with which pressure pad 112 is extended, the maximum pressure applied by pressure pad 112, various time intervals to have pressure pad 112 in an extended or retracted position, and/or the like. Parameters for electrical muscle stimulator 100B may include, for example, voltage, current, pulse amplitude, wave form, pulse frequency, pulse duration, pulse intervals, stimulation duration, and/or the like. Further, inputs 124 may allow retrieval of data, such as system usage records. Data may be stored in actuator portion 110 and/or electrical muscle stimulator 100B, for example in control electronics 119A, 119B, as well as in reader portion 120, as desired.

In an exemplary embodiment, inputs 124 comprise electronic buttons, switches, or similar devices. In other exemplary embodiments, inputs 124 comprise a communications port, for example a Universal Serial Bus (USB) port. Further, inputs 124 may comprise variable pressure control switches with corresponding indicator lights. Inputs 124 may also comprise variable speed control switches with corresponding indicator lights, on/off switches, pressure switches, click wheels, trackballs, d-pads, and/or the like. Moreover, inputs 124 may comprise any suitable components configured to allow a user to control operation of compression and stimulation system 100.

Referring again to FIG. 1, electrical muscle stimulator 100B may comprise an input 124B, control electronics 119B, an electrical pulse generator 130, and at least two electrodes 131 configured to generate an electrical pulse to a portion of a living organism suitable for any therapeutic use, preferably for generating muscle contraction. An electrical pulse may be generated according to a variety of operating parameters. Such parameters may include voltage, current, pulse amplitude, wave form, pulse frequency, pulse duration, pulse intervals, duty cycle and stimulation duration. It will be appreciated that operating parameters may suitably be varied, for example in order to achieve a desired treatment outcome.

In various exemplary embodiments, electrical pulse generator 130 is configured to generate electrical pulses for delivery to a portion of a body, for example a leg. Electrical pulse generator 130 may be configured to generate electrical pulses on a single channel; moreover, electrical pulse generator 130 may be configured to generate electrical pulses on multiple channels (for example, four channels), including simultaneously. The electrical pulses generated on a particular channel may be similar to electrical pulses generated on another channel; additionally, the pulses on a particular channel may differ from the pulses on another channel, for example with respect to voltage, amplitude, pulse width, pulse rate, and/or the like.

In various exemplary embodiments, for example wherein compression and stimulation system 100 is utilized in connection with active recovery, electrical pulse generator 130 is configured to generate an electrical output having a symmetrical biphasic waveform. Electrical pulse generator 130 may be configured to deliver an electrical pulse having an output voltage of between about 40 volts peak to peak and about 50 volts peak to peak in connection with a load of about 500 Ohms. Electrical pulse generator 130 may be configured to deliver an electrical pulse having amplitude of between about 80 milliamps and about 100 milliamps in connection with a load of about 500 Ohms. Electrical pulse generator 130 may be configured to generate an electrical pulse having a pulse width of between about 200 microseconds and about 450 microseconds. Electrical pulse generator 130 may be configured to generate an electrical pulse having a pulse rate of between about 1 Hertz and about 150 Hertz. In an exemplary embodiment, electrical pulse generator 130 is configured to generate an electrical pulse having a symmetrical biphasic waveform, a voltage of about 45 volts peak to peak, an amplitude of about 90 milliamps, a pulse width of about 400 microseconds, and a pulse rate of about 70 Hertz. In these exemplary embodiments, electrical pulse generator 130 may be configured to allow compression and stimulation system 100 to be configured with a contraction time of between about 1 second and about 60 seconds (often, about 10 seconds), a relaxation time of between about 0 seconds and about 60 seconds (often, about 15 seconds), and a ramp up/ramp down time of between about 1 seconds and about 9 seconds (often, about 2 seconds).

In certain exemplary embodiments, for example wherein compression and stimulation system 100 is utilized in connection with "Russian stimulation", electrical pulse generator 130 is configured to generate an electrical output having a symmetrical biphasic waveform. Electrical pulse generator 130 may be configured to deliver an electrical pulse having an output voltage of between about 40 volts peak to peak and about 50 volts peak to peak in connection with a load of about 500 Ohms. Electrical pulse generator 130 may be configured to deliver an electrical pulse having amplitude of between about 80 milliamps and about 100 milliamps in connection with a load of about 500 Ohms. Electrical pulse generator 130 may be configured to generate an electrical pulse having a pulse width of about 200 microseconds. Electrical pulse generator 130 may be configured to generate an electrical pulse having a pulse rate of between about 2300 Hertz and about 2700 Hertz. In an exemplary embodiment, electrical pulse generator 130 is configured to generate an electrical pulse having a symmetrical biphasic waveform, a voltage of about 45 volts peak to peak, an amplitude of about 90 milliamps, a pulse width of about 400 microseconds, a pulse rate of about 2500 Hertz on two channels, and a pulse rate of about 2550 Hertz on two channels. In these exemplary embodiments, electrical pulse generator 130 may be configured to allow compression and stimulation system 100 to be configured with a contraction time of between about 1 second and about 60 seconds (often, about 10 seconds), a relaxation time of between about 0 seconds and about 60 seconds (often, about 15 seconds), and a ramp up/ramp down time of between about 1 seconds and about 9 seconds (often, about 2 seconds).

In certain exemplary embodiments wherein compression and stimulation system 100 is utilized in an interferential mode, electrical pulse generator 130 is configured to generate an electrical output having a true sine wave waveform. Electrical pulse generator 130 may be configured to deliver an electrical pulse having an output voltage of between about 36 volts peak to peak and about 44 volts peak to peak in connection with a load of about 500 Ohms. Electrical pulse generator 130 may be configured to deliver an electrical pulse having amplitude of between about 72 milliamps and about 88 milliamps in connection with a load of about 500 Ohms. Electrical pulse generator 130 may be configured to generate an electrical pulse having a pulse width of about 100 microseconds. Electrical pulse generator 130 may be configured to generate an electrical pulse having a pulse rate of between about 1 Hertz and about 150 Hertz. In an exemplary embodiment, electrical pulse generator 130 is configured to generate an electrical pulse having a true sine wave waveform, a voltage of about 40 volts peak to peak, an amplitude of about 80 milliamps, a pulse width of about 100 microseconds, and a pulse rate of variable from between about 1 Hertz and about 150 Hertz.

In various exemplary embodiments, input 124B comprises any component or configuration that enables a user to interface with the electrical muscle stimulator 100B in order to define, redefine, or adjust pulse parameters. For example, input 124B may comprise a series of input buttons connected to control electronics 119B configured to transmit instructions thereto. In other embodiments, input 124B may comprise a touch screen or a computer configured to transmit instructions to control electronics 119B. In an exemplary embodiment, input 124B may also enable a user or medical practitioner to select pre-defined stimulation programs or create and save stimulation programs.

In various exemplary embodiments, control electronics 119B comprise any component or configuration capable of transmitting instructions to a pulse generator 130 based on instructions received from input 124B. Control electronics 119B may comprise a central processor and a memory. Control electronics 119B may also be configured to transmit instructions to reader portion 120 or alternatively to function as a reader portion 120 and transmit instructions to the actuator portion 110. In an exemplary embodiment comprising shoe 150, control electronics 119B and shoe 150 may be configured such that control electronics 119B can be housed within the sole of shoe 150, or otherwise fully contained within or integrated with shoe 150. Additional structure, features and function of control electronics 119B are described below.

In various exemplary embodiments, an electric pulse generator 130 comprises any component or configuration capable of receiving instructions from control electronics 119B, generating an electrical pulse per the instructions received from control electronics 119B, and transmitting the pulse to electrode 131. For example, pulse generator 130 may comprise an electronic oscillator and amplifier. Other components may also include a regulator, filter, rectifier, and transformer. In an exemplary embodiment comprising a shoe 150, electric pulse generator 130 may be locatable within the sole along with actuator portion 110, but embodiments wherein the electric pulse generator 130 is not integrated into a shoe is also contemplated.

Electrode 131 comprises any conductor or medium by which an electric current is conducted configured to contact a living organism, preferably in the leg and foot region, such that an electric pulse will travel from the pulse generator 130 to the living organism. For example, electrode 131 may comprise a lead 132 to conduct an electrical pulse from pulse generator 130, to a metal contact electrically connected to lead 132, and an electrically-conducting paste or gel. In certain exemplary embodiments, compression and stimulation system 100 comprises a metal connector 133 or snap, so leads 132 can detach and reattach to a metal contact so that the metal contact can be disposable and lead 132 can be reused.

In accordance with an exemplary embodiment, an electrical muscle stimulator 100B may be powered by any suitably power supply and be configured to connect to a power supply. For example, electrical muscle stimulator 100B may comprise a power input connectable to a power outlet. Alternatively, electrical muscle stimulator 100B may comprise a battery housing configured to receive a battery (not shown in figures). The types of batteries 140 as described herein may be used to power electrical muscle stimulator 100B. In an exemplary embodiment, batteries 140 used to provide power to electrical muscle stimulator 100B may be the same batteries used to power tissue depressor 100A.

In various exemplary embodiments, compression and stimulation system 100 may be at least partially operated, controlled, and/or activated by one or more electronic circuits, for example control electronics 119A, 119B. In accordance with an exemplary embodiment, control electronics 119A, 119B and/or an associated software subsystem comprise components configured to at least partially control operation of tissue depressor 100A and electrical muscle stimulator 100B. For example, control electronics 119A, 119B may comprise integrated circuits, discrete electrical components, printed circuit boards, and/or the like, and/or combinations of the same. Control electronics 119A, 119B may further comprise clocks or other timing circuitry. Control electronics 119A, 119B may also comprise data logging circuitry, for example volatile or non-volatile memories and the like, to store data, such as data regarding operation and functioning of tissue depressor 100A and electrical muscle stimulator 100B. Moreover, a software subsystem may be pre-programmed and communicate with control electronics 119A, 119B in order to adjust various variables of both tissue depressor 100A and electrical muscle stimulator 100B, for example the pulse parameters, pressure pad parameters, and coordination of the two.

Control electronics 119A, 119B may be configured to store data related to compression and stimulation system 100. For example, in various exemplary embodiments, control electronics 119A, 119B may record if compression and stimulation system 100 is mounted to the foot of a person and active, if compression and stimulation system 100 is mounted to the foot of a person and inactive, if compression and stimulation system 100 is not mounted to the foot of a person and compression and stimulation system 100 is inactive, and/or the like and/or combinations of the same.

Further, control electronics 119A, 119B may record the duration compression and stimulation system 100 is active, the number of compression or stimulation cycles performed, the parameters under which the cycles where performed by compression and stimulation system 100, and so forth. Moreover, control electronics 119A, 119B may further comprise circuitry configured to enable data stored in control electronics 119A, 119B to be retrieved for analysis, deleted, compacted, encrypted, and/or the like.

With continued reference to FIGS. 2A and 2B, in accordance with an exemplary embodiment, compression and stimulation system 100 further comprises at least one removable battery. The battery may comprise electrochemical cells suitable to provide power for the various components of compression and stimulation system 100, such as actuator portion 110, reader portion 120, and electrical pulse generator 130. Battery may be rechargeable, but may also be single-use. Batteries may comprise alkaline, nickel-metal hydride, lithium-ion, lithium-polymer, and/or other battery configurations suitable for powering actuator portion 110. Moreover, the battery may comprise any suitable chemistry, form factor, voltage, and/or capacity suitable to provide power to compression and stimulation system 100. As illustrated, battery may be decoupled from main body 102, for example to facilitate recharging of the battery, as desired. Alternatively, the battery may recharge by connecting to a power supply via a cable without having to decouple the battery from main body 102.

In accordance with an exemplary embodiment, control electronics 119A may monitor the pressure applied by pressure pad 112 when pressure pad 112 is being extended or is in a fully extended state. For example, control electronics 119A may monitor the current drawn by motor 114 and calculate the applied pressure. Alternatively, a pressure sensor may detect the applied pressure and report this value to control electronics 119A and/or an associated software subsystem.

In accordance with an exemplary embodiment, control electronics 119B may monitor the operating current, operating voltage, and/or leakage current to ensure proper and safe function of electrical muscle stimulator 100B.

Turning now to FIGS. 6A-6D, in various exemplary embodiments compression and stimulation system 100 may be configured with various power transmission components, gearings, controls, and/or the like. In an exemplary embodiment, compression and stimulation system 100 comprises depressor housing 111, pressure pad 112, pad top 113, motor 114, gears 109, slip clutch 116, and control electronics 119. Gears 109 may comprise any suitable number of and/or configuration of power transmission components configured to transfer power from motor 106 to pressure pad 112, for example spur gears, bevel gears, worm gears, and/or the like.

In various exemplary embodiments, compression and stimulation system 100 may be entirely self-contained; stated another way, compression and stimulation system 100 may be configured as a stand-alone unit wherein all components necessary for operation of compression and stimulation system 100 are contained within and/or physically coupled to depressor housing 111, and a separate reader portion 120 is not utilized.

Figure 7:
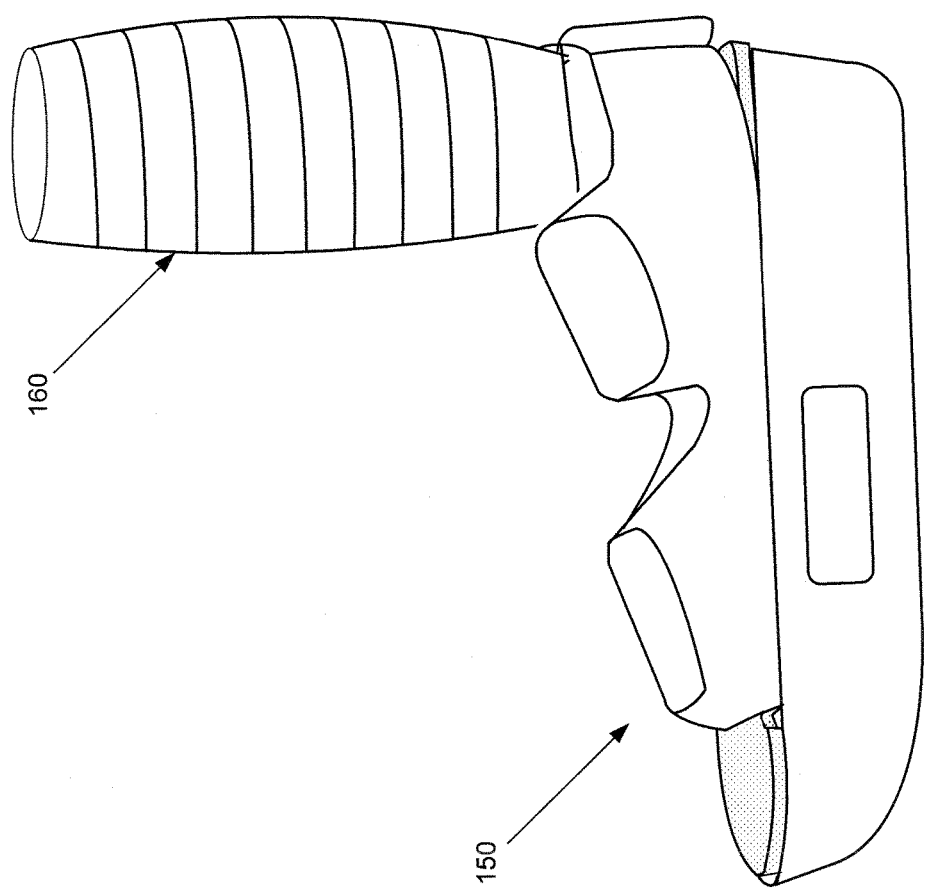
FIG. 7 illustrates an exemplary compression and stimulation system coupled to a compression garment in accordance with an exemplary embodiment.

In various exemplary embodiments, with reference to FIG. 7, compression and stimulation system 100 may be coupled to, utilized with, and/or integrated with a compression garment, for example a compression sock 160. Compression sock 160 may be configured to work in a complementary manner with compression and stimulation system 100, for example in order to treat and/or prevent deep vein thrombosis, to facilitate athletic recovery, and/or the like. In certain exemplary exemplary embodiments, electrode 131 and/or other components of compression and stimulation system 100 may be integrated into compression sock 160. In an exemplary embodiment, a compression sock 160 may be releasably coupled to a shoe 150 via one or more of zippers, snaps, straps, buttons, hooks, hook and loop fasteners, and/or the like. In other exemplary embodiments, compression sock 160 may be permanently coupled to a shoe 150, for example via gluing, stitching, and/or the like.

Compression sock 160 may comprise any suitable flexible material and may be configured with any suitable dimensions, shapes, curves, stitching, and/or the like, as desired, in order to at least partially receive and/or compress a portion of a limb. For example, compression sock 160 may be configured with any suitable level of compression, for example from between about 5 mmHg to about 50 mmHg. Also, a compression sock 160 may be configured as knee-high, as thigh-high, as pantyhose, and/or in any other suitable configuration. A compression sock 160 may also be configured to locate one or more electrodes 131 in a desired location on a leg, for example in order to facilitate stimulation of muscles of the lower leg, muscles of the upper leg, and/or the like.

In certain exemplary embodiments, compression and stimulation system 100 is configured for use in, complementary to, and/or as a substitute for low-intensity physical exertion after a workout. Stated another way, compression and stimulation system 100 is configured to facilitate "athletic recovery," or the augmentation of blood flow in the body's venous system to deliver nutrients to the muscles while simultaneously removing lactic acid and metabolic waste. After a workout, it has been found that a person may recover more quickly from the after-effects of exercise (for example, accumulation of lactates in the muscle and/or blood) via low-intensity physical exertion rather than via complete rest. The increased blood circulation attendant to low-intensity physical exertion facilitates the removal of cellular metabolic waste and lactic acid from muscle and the reduction of lactate levels in the bloodstream. Additionally, physical exertion can facilitate facilitating opening the capillary bed to enable remedial hydration and/or efficient nutrient transfer. In contrast, post-workout periods of immobility, for example either sitting or recumbent, do little physiologically to promote athletic recovery. Lowered venous peak velocity and reduced circulation closes the capillaries and locks lactic acid in place, which influences swelling and muscle soreness. Moreover, sitting with hips and knees in flexion, with bends of 60 to 90 degrees in the knees and hips, can kink the arterial blood supply and venous return, elevating the risk of edema stasis, toxin storage, and nutrient deficiency.

Therefore, by promoting blood circulation, compression and stimulation system 100 may be utilized to achieve similar benefits as those obtained via low-intensity physical exertion. For example, compression and stimulation system 100 may be utilized to achieve augmentation of peak venous velocity, augmentation of venous volume return, and/or augmentation of fibrinolysis. Additionally, the increased venous outflow evacuates cellular metabolic waste products and reduces excess fluid trapped in the soft tissues of the lower leg, thereby promoting arterial inflow to the vacated capillary bed. Lower leg edema and other significant risk factors are reduced and/or eliminated. Stated another way, via use of compression and stimulation system 100, a person may achieve similar results as those achieved via low aerobic activity such as walking but without actually walking. The user achieves augmented venous outflow despite being in a seated and/or recumbent position.

In an exemplary embodiment, compression and stimulation system 100 may be used by a person as part of a "cool down" process during the "golden hour"—approximately the first 60 minutes immediately after a workout. In other exemplary embodiments, compression and stimulation system 100 may be used during a predetermined period after a workout, for example between immediately after a workout to about 12 hours after a workout. Compression and stimulation system 100 may be utilized after a workout for a suitable duration, for example a duration of between about 10 minutes to about 2 hours, in order to assist in athletic recovery. While residual cellular metabolic waste can take several days to flush from the soft tissues, this process can be greatly accelerated via use of compression and stimulation system 100 after a workout. To facilitate use of compression and stimulation system 100 as part of an athletic recovery program, compression and stimulation system 100 or components thereof may be integrated into athletic footwear intended for use during a workout. Moreover, compression and stimulation system 100 or components thereof may also be integrated into specialized post-exercise footwear.

Compression and stimulation system 100 may be utilized on a regular schedule by a person, for example as part of a pre-workout warmup, a post-workout cooldown, and/or on days when no workout is scheduled. By increasing blood flow, compression and stimulation system 100 can facilitate improved muscle readiness prior to exercise, quicker post-exercise recovery, and/or improved circulation on days absent strenuous exercise. In particular, compression and stimulation system 100 may be desirably utilized by athletes subsequent to athletic events in order to facilitate faster recovery.

In an exemplary embodiment, actuator portion 110 is configured to repeatedly compress the venous plexus region of the foot as discussed herein. During actuating activity, electrical muscle stimulator 130 is configured to repeatedly transmit electrical pulses to the musculature surrounding or nearby to enable muscle contraction and help remove cellular metabolic waste. Electrical pulses may be generated without regard to the compression cycle of the actuator portion 110; alternatively, compression and stimulation system 100 may be programmed to coordinate the relative timing of compression cycle with the electrical pulse cycle. For example, compression and stimulation system 100 may be programmed to only generate an electrical pulse or multiple electrical pulses when pressure pad is in an extended position. Alternatively, compression and stimulation system 100 may be programmed to transmit an electrical pulse or multiple electrical pulses only during the intervals when pressure pad is retracted. Any number of schedules, protocols, and/or approaches integrating dynamic compression and electrical stimulation are considered to fall within the scope of the present disclosure.

In another exemplary embodiment, compression and stimulation system 100 is configured to compress the venous plexus region of the foot and provide electrical muscle stimulation to surrounding muscle only when the wearer of the footwear is not walking or applying weight to the footwear. In this exemplary embodiment, actuator portion 110 may be utilized for pre-workout warmup, post-workout cooldown, and/or the like, without the need for a change of footwear.

Figure 8B:
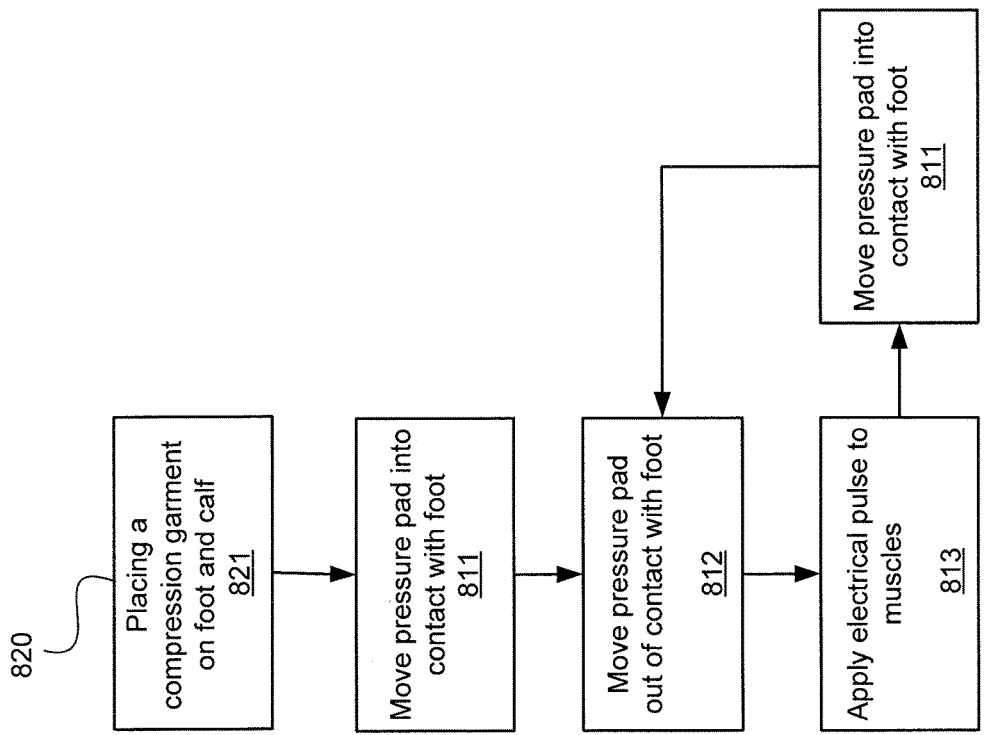
FIGS. 8A and 8B illustrate methods of using an exemplary compression and stimulation system in accordance with various exemplary embodiments.
Figure 8A:
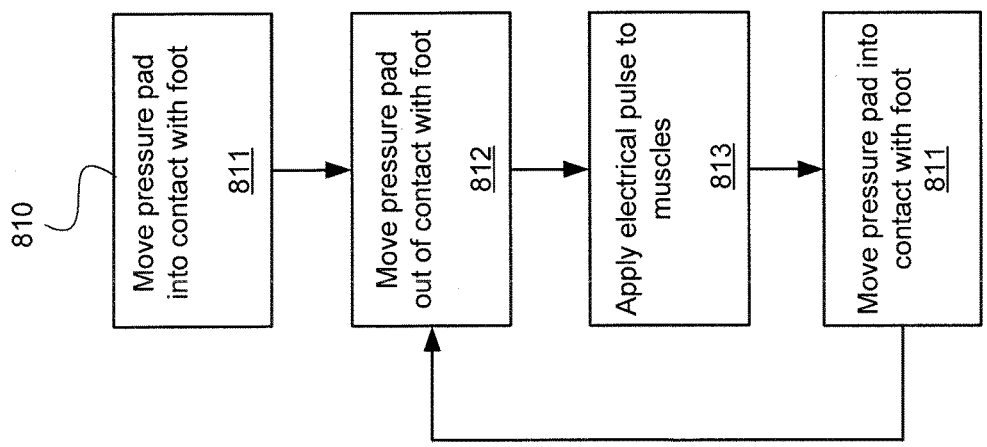

Turning now to FIG. 8A, in accordance with an exemplary embodiment a method 810 for generally enhancing circulation and/or implementing athletic recovery in a person following exercise comprises moving a pressure pad into contact with a foot (step 811), moving a pressure pad out of contact with the foot (step 812), applying an electrical pulse to lower leg muscles (step 813) and moving the pressure pad into contact with the foot (step 811). The pressure pad may be repeatedly moved as described above in order to facilitate blood flow. With reference to FIG. 8B, in accordance with an exemplary embodiment a method 820 also for enhancing circulation and/or implementing athletic recovery following exercise comprises placing a compression garment on a region of the body to be treated, such as the foot and calf (step 821), moving a pressure pad into contact with a foot (step 811), moving a pressure pad out of contact with the foot (step 812), applying an electrical pulse to lower leg muscles (step 813) and moving the pressure pad into contact with the foot (step 811), and repeating the steps 812 to 813 to 811.

Other exemplary embodiments may comprise utilizing compression and stimulation system 100 prior to an athletic event, participating in the athletic event, and utilizing compression and stimulation system 100 subsequent to the athletic event. Each of these steps may comprise any suitable use of compression and stimulation system 100, for example method 810 or 820. Moreover, these steps may be performed at any suitable time prior to and/or subsequent to the athletic event, and compression and stimulation system 100 may be utilized for any desired length of time (for example, 15 minutes, 30 minutes, one hour, and/or the like). Moreover, compression and stimulation system 100 may be utilized for a length of time specified by a physician.

In various exemplary embodiments, compression and stimulation system 100 is configured for use by individuals who are in fixed, standing, and/or sitting positions for extended periods of time, for example office workers, pregnant women, passengers on long-haul airline flights in excess of four hours, individuals in wheelchairs, service workers whose positions require standing, hospital patients, and/or the like. By improving blood flow in the lower extremities and legs, compression and stimulation system 100 can reduce the negative health impacts associated with extended standing, extended sitting, and/or reduced mobility or immobility of a portion of the body. Moreover, compression and stimulation system 100 may be configured for use in connection with the removal of metabolic waste, wound care and recovery, or the treatment of medical conditions including plantar fasciitis, restless leg syndrome, deep vein thrombosis, pulmonary embolism, and venous insufficiency.

In various exemplary embodiments, with reference now to FIG. 9, compression and stimulation system 100 may be utilized in connection with treatment of plantar fasciitis. In these embodiments, activation of compression and stimulation system 100 is not primarily directed to increasing circulation and/or vascularity (though these results may be present); rather, activation of compression and stimulation system 100 is directed to stretching, massaging, and/or otherwise treating the plantar fascia and/or the surrounding tissue and components of the foot. In an exemplary embodiment, compression and stimulation system 100 is utilized to stretch the plantar fascia via extension of pressure pad 112 and/or via delivery of an electrical pulse by electric stimulator 100B.

In an exemplary embodiment, in connection with a method 910 for treating plantar fasciitis, pressure pad 112 is extended into contact with a foot in order to stretch the plantar fascia. Pressure pad 112 may be placed in contact with a foot (step 911) for a desired period of time in order to stretch the plantar fascia. In accordance with an exemplary embodiment, when moved to the fully extended position, pressure pad 112 may generate a pressure between about 1 mmHg and 250 mmHg against the person's foot. Further, pressure pad 112 may be extended with a force between about 25 Newtons and 80 Newtons in certain exemplary embodiments. Pressure pad 112 may be kept in an extended position for a time between about 1 second and about 6 seconds. Pressure pad 112 is then retracted (step 912). Pressure pad 112 may then be re-extended (step 913), such as after a delay of between about 10 and 60 seconds. However, other time frames can be used, and all suitable time frames are thought to fall within the scope of the present disclosure. During either extension or retraction of pressure pad 112, an electrical pulse may be applied to a portion of the body, for example the lower leg muscles, the top of the foot, the bottom of the foot, and/or the like (step 914).

In various exemplary embodiments, when utilized for treatment of plantar fasciitis, compression and stimulation system 100 may be utilized any suitable number of times in a day. In an exemplary embodiment, compression and stimulation system 100 is used for treatment of plantar fasciitis once a day. In another exemplary embodiment, compression and stimulation system 100 is used for treatment of plantar fasciitis twice a day. Moreover, compression and stimulation system 100 may also be used more than twice a day, on alternating days, and/or on any other suitable time schedule, as desired.

In various exemplary embodiments, when utilized for treatment of plantar fasciitis, compression and stimulation system 100 may be utilized for any suitable duration. In an exemplary embodiment, compression and stimulation system 100 is used for treatment of plantar fasciitis for about 30 minutes at a time. In another exemplary embodiment, compression and stimulation system 100 is used for treatment of plantar fasciitis for about one hour at a time. Moreover, compression and stimulation system 100 may be used for between about fifteen minutes and about eight hours at a time, and/or for any other suitable duration, as desired.

Turning now to FIG. 10, in various exemplary embodiments, compression and stimulation system 100 may be utilized in connection with treatment of deep vein thrombosis and/or prevention of pulmonary embolism. In these embodiments, activation of compression and stimulation system 100 may be primarily directed to increasing venous peak velocity. Additionally, improved circulation and/or vascularity may be achieved. In an exemplary embodiment, compression and stimulation system 100 is utilized to increase venous peak velocity via extension of pressure pad 112 and/or via delivery of an electrical pulse by electric stimulator 100B.

In an exemplary embodiment, in connection with a method 1010 for treatment of deep vein thrombosis and/or prevention of pulmonary embolism, pressure pad 112 is extended into contact with a foot in order to force blood through the venous plexus. Pressure pad 112 may be placed in contact with a foot (step 1011) for a desired period of time in order to force blood through the venous plexus. In accordance with an exemplary embodiment, when moved to the fully extended position, pressure pad 112 may generate a pressure between about 1 mmHg and 500 mmHg against the person's foot. Further, pressure pad 112 may be extended with a force between about 50 Newtons and 125 Newtons in certain exemplary embodiments. Pressure pad 112 may be kept in an extended position for a time between about 1 and 3 seconds. Pressure pad 112 is then retracted (step 1012). Pressure pad 112 may then be re-extended (step 1013), such as after a delay of between about 20 and 40 seconds. However, other time frames can be used, and all suitable time frames are thought to fall within the scope of the present disclosure. During either extension or retraction of pressure pad 112, an electrical pulse may be applied to a portion of the body, for example the upper leg muscles, the lower leg muscles, the top of the foot, the bottom of the foot, and/or the like (step 1014).

In various exemplary embodiments, in connection with a method 1010 for treatment of deep vein thrombosis and/or prevention of pulmonary embolism, extension of pressure pad 112 is configured to raise the peak femoral venous velocity in a patient via compression of the venous plexus. In an exemplary embodiment, compression of the venous plexus via extension of pressure pad 112, either together with or independent of delivery of an electrical pulse to a portion of the body, results in peak femoral venous velocity in excess of 30 centimeters per second (cm/s). In another exemplary embodiment, compression of the venous plexus via extension of pressure pad 112, either together with or independent of delivery of an electrical pulse to a portion of the body, results in peak femoral venous velocity in excess of 40 cm/s. In another exemplary embodiment, compression of the venous plexus via extension of pressure pad 112, either together with or independent of delivery of an electrical pulse to a portion of the body, results in peak femoral venous velocity in excess of 45 cm/s. Moreover, compression and stimulation system 100 may be utilized to compress the venous plexus (and/or deliver an electrical pulse to a portion of the body) in order to achieve any suitable peak femoral venous velocity in a patient, and the foregoing examples are by way of illustration and not of limitation.

In various exemplary embodiments, when utilized for treatment of deep vein thrombosis and/or prevention of pulmonary embolism, compression and stimulation system 100 may be utilized any suitable number of times in a day. In an exemplary embodiment, compression and stimulation system 100 is used for treatment of treatment of deep vein thrombosis and/or prevention of pulmonary embolism once a day. In another exemplary embodiment, compression and stimulation system 100 is used for treatment of deep vein thrombosis and/or prevention of pulmonary embolism twice a day. Moreover, compression and stimulation system 100 may also be used more than twice a day, on alternating days, continuously, and/or on any other suitable time schedule, as desired.

In various exemplary embodiments, when utilized for treatment of deep vein thrombosis and/or prevention of pulmonary embolism, compression and stimulation system 100 may be utilized for any suitable duration. In an exemplary embodiment, compression and stimulation system 100 is used 24 hours a day. In another exemplary embodiment, compression and stimulation system 100 is used for treatment of deep vein thrombosis and/or prevention of pulmonary embolism for about 12 hours at a time. Moreover, compression and stimulation system 100 may be used for between about three hours and about 6 hours at a time, and/or for any other suitable duration, as desired.

Turning now to FIG. 11, in various exemplary embodiments, compression and stimulation system 100 may be utilized in connection with treatment of restless leg syndrome. In these embodiments, use of compression and stimulation system 100 may be directed to increasing blood flow in the foot and/or leg, stimulation of nerves in the foot and/or leg, and/or the like. Additionally, improved circulation and/or vascularity may be achieved. In an exemplary embodiment, compression and stimulation system 100 is utilized to stimulate the foot via extension of pressure pad 112 and/or stimulate a portion of the body via delivery of an electrical pulse by electric stimulator 100B.

In an exemplary embodiment, in connection with a method 1110 for treating restless leg syndrome, pressure pad 112 is extended into contact with a foot in order to stimulate the foot. Pressure pad 112 may be placed in contact with a foot (step 1111) for a desired period of time in order to stimulate the foot. In accordance with an exemplary embodiment, when moved to the fully extended position, pressure pad 112 may generate a pressure between about 1 mmHg and 300 mmHg against the person's foot. Further, pressure pad 112 may be extended with a force between about 25 Newtons and 75 Newtons in certain exemplary embodiments. Pressure pad 112 may be kept in an extended position for a time between about 1 and 3 seconds. Pressure pad 112 is then retracted (step 1112). Pressure pad 112 may then be re-extended (step 1113), such as after a delay of between about 20 and 30 seconds. However, other time frames can be used, and all suitable time frames are thought to fall within the scope of the present disclosure. During either extension or retraction of pressure pad 112, an electrical pulse may be applied to a portion of the body, for example the upper leg muscles, the lower leg muscles, the top of the foot, the bottom of the foot, and/or the like (step 1114).

In various exemplary embodiments, when utilized for treatment of restless leg syndrome, compression and stimulation system 100 may be utilized any suitable number of times in a day. In an exemplary embodiment, compression and stimulation system 100 is used for treatment of restless leg syndrome once a day, for example between about 1 hour and about 3 hours before retiring to bed. In another exemplary embodiment, compression and stimulation system 100 is used for treatment of restless leg syndrome twice a day, for example within about 1 hour and about 3 hours of arising in the morning, and between about 1 hour and about 3 hours before retiring to bed. Moreover, compression and stimulation system 100 may also be used more than twice a day, on alternating days, and/or on any other suitable time schedule, as desired. In certain exemplary embodiments, compression and stimulation system 100 may be utilized on an "as-needed" basis to treat symptoms of restless leg syndrome in real-time as they are occurring.

In various exemplary embodiments, when utilized for treatment of restless leg syndrome, compression and stimulation system 100 may be utilized for any suitable duration. In an exemplary embodiment, compression and stimulation system 100 is used for treatment of restless leg syndrome for between about one hour and about three hours at a time. Moreover, compression and stimulation system 100 may be used for any other suitable duration, as desired.

Turning now to FIG. 12, in various exemplary embodiments, compression and stimulation system 100 may be utilized in connection with treatment of edema. In these embodiments, activation of compression and stimulation system 100 may be directed to increasing circulation and/or vascularity in a portion of a human body. In an exemplary embodiment, compression and stimulation system 100 is utilized to compress the venous plexus region of the foot via extension of pressure pad 112 and/or stimulate a portion of the body via delivery of an electrical pulse by electric stimulator 100B.

In an exemplary embodiment, in connection with a method 1210 for treating edema, pressure pad 112 is extended into contact with a foot in order to force blood from the venous plexus region of the foot. Pressure pad 112 may be placed in contact with a foot (step 1211) for a desired period of time in order to force blood from the venous plexus. In accordance with an exemplary embodiment, when moved to the fully extended position, pressure pad 112 may generate a pressure between about 1 mmHg and 500 mmHg against the person's foot. Further, pressure pad 112 may be extended with a force between about 25 Newtons and 125 Newtons in certain exemplary embodiments. Pressure pad 112 may be kept in an extended position for a time between about 1 second and about 5 seconds. Pressure pad 112 is then retracted (step 1212) in order to allow the venous plexus to at least partially refill with blood. Pressure pad 112 may then be re-extended (step 1213) to force blood from the venous plexus, such as after a delay of between about 30 seconds and about 60 seconds. However, other time frames can be used, and all suitable time frames are thought to fall within the scope of the present disclosure. During either extension or retraction of pressure pad 112, an electrical pulse may be applied to a portion of the body, for example the upper leg muscles, the lower leg muscles, the top of the foot, the bottom of the foot, and/or the like (step 1214).

In various exemplary embodiments, when utilized for treatment of edema, compression and stimulation system 100 may be utilized any suitable number of times in a day. In an exemplary embodiment, compression and stimulation system 100 is used for treatment of edema once a day. In another exemplary embodiment, compression and stimulation system 100 is used for treatment of edema twice a day. Moreover, compression and stimulation system 100 may also be used more than twice a day, on alternating days, and/or on any other suitable time schedule, as desired. In certain exemplary embodiments, compression and stimulation system 100 may be utilized on an "as-needed" basis to treat symptoms of edema in real-time, for example responsive to patient discomfort.

In various exemplary embodiments, when utilized for treatment of edema, compression and stimulation system 100 may be utilized for any suitable duration. In an exemplary embodiment, compression and stimulation system 100 is used for treatment of edema for between about one hour and about eight hours at a time. Moreover, compression and stimulation system 100 may be used for any other suitable duration, as desired.

Turning now to FIG. 13, in various exemplary embodiments, compression and stimulation system 100 may be utilized in connection with treatment of venous insufficiency. In these embodiments, activation of compression and stimulation system 100 may be directed to increasing circulation, counteracting the effect of damaged valves in one or more veins, and/or the like. In an exemplary embodiment, compression and stimulation system 100 is utilized to compress the venous plexus region of the foot via extension of pressure pad 112 and/or stimulate a portion of the body via delivery of an electrical pulse by electric stimulator 100B.

In an exemplary embodiment, in connection with a method 1310 for treating venous insufficiency, pressure pad 112 is extended into contact with a foot in order to force blood from the venous plexus region of the foot. Pressure pad 112 may be placed in contact with a foot (step 1311) for a desired period of time in order to force blood from the venous plexus. In accordance with an exemplary embodiment, when moved to the fully extended position, pressure pad 112 may generate a pressure between about 1 mmHg and 500 mmHg against the person's foot. Further, pressure pad 112 may be extended with a force between about 25 Newtons and 125 Newtons in certain exemplary embodiments. Pressure pad 112 may be kept in an extended position for a time between about 1 second and about 5 seconds. Pressure pad 112 is then retracted (step 1312) in order to allow the venous plexus to at least partially refill with blood. Pressure pad 112 may then be re-extended (step 1313) to force blood from the venous plexus, such as after a delay of between about 30 seconds and about 60 seconds. However, other time frames can be used, and all suitable time frames are thought to fall within the scope of the present disclosure. During either extension or retraction of pressure pad 112, an electrical pulse may be applied to a portion of the body, for example the upper leg muscles, the lower leg muscles, the top of the foot, the bottom of the foot, and/or the like (step 1314).

In various exemplary embodiments, when utilized for treatment of venous insufficiency, compression and stimulation system 100 may be utilized any suitable number of times in a day. In an exemplary embodiment, compression and stimulation system 100 is used for treatment of venous insufficiency once a day. In another exemplary embodiment, compression and stimulation system 100 is used for treatment of venous insufficiency twice a day. Moreover, compression and stimulation system 100 may also be used more than twice a day, on alternating days, and/or on any other suitable time schedule, as desired. In certain exemplary embodiments, compression and stimulation system 100 may be utilized on an "as-needed" basis to treat symptoms of venous insufficiency in real-time, for example responsive to patient discomfort.

In various exemplary embodiments, when utilized for treatment of venous insufficiency, compression and stimulation system 100 may be utilized for any suitable duration. In an exemplary embodiment, compression and stimulation system 100 is used for treatment of venous insufficiency for between about one hour and about twelve hours at a time. Moreover, compression and stimulation system 100 may be used for any other suitable duration, as desired.

Turning now to FIG. 14, in various exemplary embodiments, compression and stimulation system 100 may be utilized in connection with treatment of wounds. In these embodiments, activation of compression and stimulation system 100 may be directed to increasing blood circulation and/or vascularity at and/or around a wound site. Moreover, in connection with wound care, use of compression and stimulation system 100 may be guided and/or governed by the circulatory capacity of the body in the region of a wound. Stated another way, compression and stimulation system 100 may be configured to increase circulation in the region of a wound without exceeding the circulatory capacity of the region of the wound. In an exemplary embodiment, compression and stimulation system 100 is utilized to compress a portion of the body, for example the venous plexus region of the foot, via extension of pressure pad 112; additionally, compression and stimulation system 100 may be utilized to stimulate a portion of the body via delivery of an electrical pulse by electric stimulator 100B.

In an exemplary embodiment, in connection with a method 1410 for wound care, pressure pad 112 is extended into contact with a portion of a body, for example a foot, in order to force blood from the portion of the body and/or otherwise assist in "pumping" blood through a region of the body. Pressure pad 112 may be placed in contact with the body (step 1411) for a desired period of time in order to force blood therethrough. In accordance with an exemplary embodiment, when moved to the fully extended position, pressure pad 112 may generate a pressure between about 1 mmHg and 200 mmHg against the body. Further, pressure pad 112 may be extended with a force between about 12 Newtons and 75 Newtons in certain exemplary embodiments. Pressure pad 112 may be kept in an extended position for a time between about 1 second and about 5 seconds. Pressure pad 112 is then retracted (step 1412) in order to allow the portion of the body to at least partially refill with blood. Pressure pad 112 may then be re-extended (step 1413) to force blood from the portion of the body, such as after a delay of between about 30 seconds and about 60 seconds. However, other time frames can be used, and all suitable time frames are thought to fall within the scope of the present disclosure. During either extension or retraction of pressure pad 112, an electrical pulse may be applied to a portion of the body, for example the upper arm muscles, the lower arm muscles, the upper leg muscles, the lower leg muscles, the top of the foot, the bottom of the foot, and/or the like (step 1414).

In various exemplary embodiments, when utilized for wound care, compression and stimulation system 100 may be utilized any suitable number of times in a day. In an exemplary embodiment, compression and stimulation system 100 is used for wound care once a day. In another exemplary embodiment, compression and stimulation system 100 is used for wound care twice a day. Moreover, compression and stimulation system 100 may also be used more than twice a day, on alternating days, and/or on any other suitable time schedule, as desired. In certain exemplary embodiments, compression and stimulation system 100 may be utilized on a continuous basis to provide a steadily elevated level of circulation in the region of a wound.

In various exemplary embodiments, when utilized for wound care, compression and stimulation system 100 may be utilized for any suitable duration. In an exemplary embodiment, compression and stimulation system 100 is used for wound care for between about one hour and about twenty-four hours at a time. Moreover, compression and stimulation system 100 may be used for any other suitable duration, as desired.

It will be appreciated that various steps of the foregoing methods, for example extending a pressure pad into contact with a portion of the body, removing a pressure pad from contact with a portion of the body, applying an electrical stimulation to a portion of the body, and so forth, may be repeated as suitable in order achieve a desired outcome.

The present disclosure has been described above with reference to various exemplary embodiments. However, those skilled in the art will recognize that changes and modifications may be made to the exemplary embodiments without departing from the scope of the present disclosure. For example, the various operational steps, as well as the components for carrying out the operational steps, may be implemented in alternate ways depending upon the particular application or in consideration of any number of cost functions associated with the operation of the system, e.g., one or more of the steps may be deleted, modified, or combined with other steps. Further, it should be noted that while the methods and systems for compression described above are suitable for use on the foot, similar approaches may be used on the hand, calf, or other areas of the body. These and other changes or modifications are intended to be included within the scope of the present disclosure.

Moreover, as will be appreciated by one of ordinary skill in the art, principles of the present disclosure may be reflected in a computer program product on a tangible computer-readable storage medium having computer-readable program code means embodied in the storage medium. Any suitable computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions. These computer program instructions may also be stored in a computer-readable memory that can direct a computer or other programmable data processing apparatus to function in a particular manner, such that the instructions stored in the computer-readable memory produce an article of manufacture including instruction means which implement the function specified. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified.

In the foregoing specification, the disclosure has been described with reference to various embodiments. However, one of ordinary skill in the art appreciates that various modifications and changes can be made without departing from the scope of the present disclosure as set forth in the claims below. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. Further, when language similar to "at least one of A, B, or C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A compression and stimulation system, comprising:
   an actuator portion comprising a pressure pad;
   a software subsystem; and
   an electrical stimulation portion comprising a pulse generator and at least two electrodes which is operatively controlled by the software subsystem;
   wherein the software subsystem is programmed to prevent delivery of an electrical pulse from the at least two electrodes responsive to an indication that the electrical stimulation portion has been moved within a predetermined time period.

2. The system of claim 1, wherein the actuator portion is completely containable within an item of footwear.

3. The system of claim 2, further comprising the item of footwear, wherein the footwear has a flexible sole.

4. The system of claim 3, further comprising power supply, wherein the power supply supplies operational power to the actuator portion and to the electrical stimulation portion.

5. The system of claim 3, wherein the actuator portion is removable from the item of footwear.

6. The system of claim 3, wherein the electrical stimulation portion is removable from the item of footwear.

7. The system of claim 1, further comprising a sensor operable to communicate with the actuator portion, wherein the sensor determines whether a user of the system is walking, and wherein, responsive to input from the sensor, the actuator portion is not activated when the user of the system is walking.

8. The system of claim 7, wherein the actuator portion is configured to prevent extension of the pressure pad responsive to an indication that the actuator portion has been moved within a predetermined time.

9. The system of claim 1, wherein the pressure pad extends a distance between 1 mm and 24 mm to generate an applied pressure of between 100 mmHg and 500 mmHg.

10. The system of claim 9, wherein the actuator portion extends the pressure pad from a fully retracted position to a fully extended position in a time between about 100 milliseconds and about 300 milliseconds.

11. A compression and stimulation system, comprising:
    an item of footwear comprising a flexible sole for walking thereon;
    an actuator portion comprising a pressure pad, the actuator portion completely contained within the item of footwear;
    a compression garment coupled to the item of footwear; and
    an electrical stimulation portion coupled to the compression garment, the electrical stimulation portion comprising a pulse generator and at least two electrodes;
    wherein the electrical stimulation portion is in operative communication with the actuator portion; and
    wherein the electrical stimulation portion is configured to coordinate the relative timing of a compression cycle with an electrical pulse cycle.

12. The system of claim 11, further comprising a power supply electrically coupled to both the actuator portion and the electrical stimulation portion.

13. The system of claim 12, wherein the power supply is completely contained within the item of footwear.

14. The system of claim 11, wherein the pulse generator delivers an electrical pulse for application to a portion of a body by the at least two electrodes, the electrical pulse having a voltage of about 40 volts, an amplitude of about 90 milliamps, a pulse width of about 400 microseconds, and a pulse rate of about 70 Hertz.

15. A foot compression system, comprising:
    an actuator portion configured to deliver a compressive force to the venous plexus region of the foot, wherein the actuator portion comprises a retractable pressure pad;
    a reader portion configured to transmit commands to the actuator portion;
    a software subsystem; and
    an electrical stimulation portion comprising a pulse generator and at least two electrodes which is operatively controlled by the software subsystem;
    wherein the software subsystem is programmed to delay delivery of an electrical pulse from the at least two electrodes responsive to an indication that the electrical stimulation portion is moving.

16. The foot compression system of claim 15, wherein at least one of the actuator portion and the electrical stimulation portion is completely contained within an item of footwear.

17. The foot compression system of claim 15, wherein at least one of the actuator portion and the electrical stimulation portion is removable from the item of footwear.

18. The foot compression system of claim 15, further comprising a compression garment coupled to the electrical stimulation portion.

* * * * *